US012565522B2

(12) United States Patent
Xu et al.

(10) Patent No.: US 12,565,522 B2
(45) Date of Patent: Mar. 3, 2026

(54) MICROPEPTIDE HMMW AND APPLICATION THEREOF

(71) Applicant: NANJING ANJI BIOTECHNOLOGY CO., LTD., Jiangsu (CN)

(72) Inventors: Hanmei Xu, Jiangsu (CN); Mengwei Li, Jiangsu (CN)

(73) Assignee: NANJING ANJI BIOTECHNOLOGY CO., LTD., Jiangsu (CN)

( * ) Notice: Subject to any disclaimer, the term of this patent is extended or adjusted under 35 U.S.C. 154(b) by 809 days.

(21) Appl. No.: 17/640,367

(22) PCT Filed: Nov. 3, 2020

(86) PCT No.: PCT/CN2020/126072
§ 371 (c)(1),
(2) Date: Mar. 4, 2022

(87) PCT Pub. No.: WO2021/043341
PCT Pub. Date: Mar. 11, 2021

(65) Prior Publication Data
US 2022/0340623 A1        Oct. 27, 2022

(30) Foreign Application Priority Data

Sep. 5, 2019    (CN) ......................... 201910850262.X

(51) Int. Cl.
| | |
|---|---|
| *C07K 14/47* | (2006.01) |
| *A61K 38/00* | (2006.01) |
| *A61P 35/00* | (2006.01) |
| *C12N 15/85* | (2006.01) |
| *C12Q 1/6851* | (2018.01) |
| *C12Q 1/6886* | (2018.01) |

(52) U.S. Cl.
CPC .............. *C07K 14/47* (2013.01); *A61P 35/00* (2018.01); *C12N 15/85* (2013.01); *C12Q 1/6886* (2013.01); *A61K 38/00* (2013.01); *C12N 2800/107* (2013.01); *C12Q 1/6851* (2013.01); *C12Q 2600/158* (2013.01)

(58) Field of Classification Search
CPC ......... C07K 14/47; A61P 35/00; C12N 15/85; C12N 2800/107; C12Q 1/6886; C12Q 1/6851; C12Q 2600/158; A61K 38/00
See application file for complete search history.

(56) References Cited

PUBLICATIONS

Drumm et al, Genetic Variation and Clinical Heterogeneity in Cystic Fibrosis, Annu. Rev. Pathol. Mech. Dis., 2012, 7, pp. 267-282.*
Yampolsky et al, The Exchangeability of Amino Acids in Proteins, Genetics, 2005, 170, pp. 1459-1472.*
Cellular and Molecular Basis of Cancer-Merck Manual, from http://www.merckmanuals.com/professional/print/hematology_and_oncology/overview_of . . . , 2008, pp. 1-5.*
Li et al, Micropeptide MIAC Inhibits HNSCC Progression by Interacting with Aquaporin 2, J. Am. Chem. Soc., 2020, 142, pp. 6708-6716.*
Huang et al, A Peptide Encoded by a Putative lncRNA HOXB-AS3 Suppresses Colon Cancer Growth, Molecular Cell, 2017, 68, pp. 171-184.*
Higgins, Desmond G. et al—Clustal: A Package for Performing Multiple Sequence Alignment on a Microcomputer, Gene 73 (1988)237-244—Elsevier.
International Search Report issued Feb. 4, 2021 for PCT/CN2020/126072.
Oh JH et al. "GenBank Accession No. NR_ 110590.1" 4-10—NCBI, May 24, 2018 (May 24, 2018), See Origin section and Reference section.
Li, M. et al. "GenBank Accession No. MN872799.1"—GenBankNCBI, Oct. 12, 2020 (Oct. 12, 2020), see entire document.
Li, M. et al. "GenBank Accession No. QOI14795.1"—NCBI, Oct. 12, 2020 (Oct. 12, 2020), see entire document.

* cited by examiner

*Primary Examiner* — Li N Komatsu
(74) *Attorney, Agent, or Firm* — Schmeiser, Olsen & Watts LLP

(57)        ABSTRACT

A micropeptide HMMW of a new structure and an application thereof, and relates to the field of biomedical research and development is provided. The micropeptide HMMW is obtained by encoding human lncRNA, and a recombinant vector is constructed so that objective cells perform high expression on the micropeptide HMMW, which can inhibit proliferation and migration of multiple solid tumors including the head and neck cancer, thyroid cancer, lung cancer, esophageal squamous cell carcinoma, stomach cancer, breast cancer, kidney cancer, skin cancer and the like, and growth of tumors in the body. The micropeptide HMMW has potential value for new drug development, important tumor detection and treatment value.

1 Claim, 10 Drawing Sheets

Specification includes a Sequence Listing.

A549 cells of lung cancer

TE13 cells of esophageal squamous carcinoma

MGC803 cells of stomach cancer

MDA-MB-231 cells of breast cancer

UOK262 cells of kidney cancer

A431 cells of skin cancer

MICROPEPTIDE HMMW AND APPLICATION THEREOF

CROSS-REFERENCE TO RELATED APPLICATIONS

This application claims priority to PCT Application No. PCT/CN2020/126072, having a filing date of Nov. 3, 2020, which is based on CN Application No. 201910850262. X, having a filing date of Sep. 5, 2019, the entire contents both of which are hereby incorporated by reference.

SEQUENCE LISTING

This application includes a separate sequence listing in complicance with the requirements of 37 C.F.R. §§ 1.824 (a)(2)-1.824(a)(6) and 1.824(b), submitted under the file name "0069US01_SEQUENCE_LISTING", created on Mar. 3, 2022, having a file size of 11 KB, the contents of which are hereby incorporated by reference.

FIELD OF TECHNOLOGY

The following pertains to the field of biomedical research and development and more specifically, relates to an application of novel micropeptide HMMW in tumor detection and treatment.

BACKGROUND

With the development of transcriptomic, proteomic and bioinformatics analysis methods, scientists have discovered that those previously defined as non-coding RNA molecules (such as lncRNAs, circRNAs and miRNAs) actually contain small open reading frames (sORFs, with a nucleotide sequence of not more than 300 bp) with an encoding ability. sORF-encoded peptides (SEPs) are called micropeptides (not more than 100 amino acids in length). In 2015, on the journal *Cell*, scientists screened the skeletal muscle-specific lncRNA encoding peptide Myoregulin (MLN) by the bioinformatics method, and determined that MLN is an important regulator of skeletal muscle physiology. In the past two years, there are not many reports about lncRNA encoding micropeptides in the world, and the research focuses on muscle differentiation and skeletal muscle development. Therefore, discovering and identifying new micropeptides encoded by lncRNA and exploring new application fields are of great significance for opening the door of encoding non-coding RNAs.

Tumors are malignant diseases that seriously endanger human life and health. Unlimited growth, invasion and metastasis are the malignant signs of tumors and the main causes of treatment failure and death. At present, the main clinical treatment methods for cancer patients are operative therapy and chemotherapy (chemotherapy/drug therapy). For most tumors, operative therapy is suitable for curative treatment of early, intermediate and localized tumors and palliative treatment of advanced tumors. Although there is no chemotherapy resistance or radioresistance in surgical treatment, it is more traumatic, difficult to operate in some parts, and ineffective to subclinical metastases. For most tumors, chemotherapy is suitable for intermediate and advanced tumors, and as a systemic treatment, chemotherapy has therapeutic effects on primary tumors, metastases and subclinical metastases. However, chemotherapeutic drugs have poor selectivity. While achieving a therapeutic effect, toxic and side effects in various degrees often occur;

and cancer patients who receive chemotherapy for a long time may develop new malignant tumors due to immunosuppressive effects and direct carcinogenic effects.

Owing to the advantages of high specificity, small toxic and side effects, clear mechanism of action, and no harm to normal cells, tissues and organs, the application of peptide drugs in the treatment of cancers, cardiovascular diseases, immune-related diseases, metabolic diseases and infectious diseases has been gradually developed. At present, there are more than 80 peptide drugs on the market in the world, with total annual sales of more than 20 billion US dollars. Although the market sales of peptide drugs in China maintain a momentum of rapid growth, most of them are generic peptide drugs.

At present, the research on micropeptides in the detection and treatment of malignant tumors such as head and neck cancer, thyroid cancer, lung cancer and esophageal squamous cell carcinoma is still blank. Through bioinformatics analysis and experimental verification, embodiments of the present invention have discovered a new micropeptide in tumors and explored its application in tumor detection and treatment, providing a new solution for tumor detection and treatment.

SUMMARY

An aspect relates to a novel micropeptide HMMW and its amino acid sequences. Micropeptide HMMW is a new human endogenous peptide discovered for the first time;

A second aspect of embodiments of the present invention is to provide a nucleotide, and the nucleotide sequence can encode the obtained micropeptide HMMW;

A third aspect of embodiments of the present invention is to provide a recombinant vector containing the nucleotide sequence encoding micropeptide HMMW;

A fourth aspect embodiments of the present invention is to apply micropeptide HMMW or nucleotide encoding the micropeptide HMMW in the preparation of tumor detection reagents and treatment drugs, specifically including detection and treatment of head and neck cancer, thyroid cancer, lung cancer, esophageal squamous cell carcinoma, stomach cancer, breast cancer, kidney cancer and skin cancer.

Embodiments of the present invention adopt the following technical solution:

Application of a novel micropeptide HMMW in the preparation of tumor detection reagents and/or tumor treatment drugs, wherein the amino acid sequences of the micropeptide HMMW contain a sequence shown in SEQ ID NO: 2

Application of a novel micropeptide HMMW in the preparation of tumor detection reagents or tumor treatment drugs, wherein the amino acid sequences of the micropeptide HMMW have at least 85% homology to the amino acid sequence shown in SEQ ID NO: 1 (micropeptide HMMW I) (as shown in SEQ ID NO: 2 and SEQ ID NO: 3, the corresponding micropeptides are named HMMW II and HMMW III), or have at least 90% homology (as shown in SEQ ID NO: 4 and SEQ ID NO: 5, the corresponding micropeptides are named HMMW IV and HMMW V), or have at least 95% homology (as shown in SEQ ID NO: 6 and SEQ ID NO: 7, the corresponding micropeptides are named HMMW VI and HMMW VII), or have at least 98% homology (as shown in SEQ ID NO: 8 and SEQ ID NO: 9, the corresponding micropeptides are named HMMW VIII and HMMW IX), and these sequences with homology to SEQ ID NO: 1 retain similar functions of inhibiting tumor cell growth, proliferation, invasion or migration and can be used to prepare tumor detection reagents or tumor treatment drugs.

"Homology" described herein refers to the percentage of similarity in a comparison of two or more amino acid sequences. The percentage of similarity can be determined electronically, such as by the MEGALIGN program (Laser-gene software package, DNASTAR, Inc., Madison Wis.). The MEGALIGN program can compare two or more sequences according to different methods such as the Cluster method (Higgins, D. G. and P. M. Sharp (1988) Gene 73: 237-244). The Cluster method arranges groups of sequences into clusters by examining the distances between all pairs. The clusters are then assigned in pairs or groups. The percentage of homology between two amino acid sequences such as Sequence A and Sequence B is calculated with the following formula:

(Number of residues matching between sequence *A* and sequence *B*\*100)/(Number of residues in sequence *A*−Number of interval residues in sequence *A*−Number of interval residues in sequence *B*).

Application of a novel micropeptide HMMW in the preparation of tumor detection reagents or tumor treatment drugs, wherein the novel micropeptide HMMW contains an amino acid sequence shown in SEQ ID NO: 1.

A nucleotide, wherein the nucleotide is any of a, b and c:

(a) A nucleotide encoding micropeptide HMMW contain-ing the amino acid sequence shown in SEQ ID NO: 1;

(b) A nucleotide encoding micropeptide HMMW having at least 85% homology to the amino acid sequence shown in SEQ ID NO: 1;

(c) Nucleotide sequences encoding the amino acids described herein, specifically the nucleotide sequences shown in SEQ ID NO: 10 to NO: 18 (N is any of A/T/G/C).

A recombinant vector, wherein the recombinant vector contains any of the foregoing nucleotides.

Application of any of the foregoing nucleotides in the preparation of tumor detection reagents and/or tumor treat-ment drugs.

A tumor detection kit, wherein the kit contains a specific primer pair for any of the foregoing nucleotide sequences.

According to embodiments, sequences of the specific primer pair are shown in SEQ ID NO: 19 and SEQ ID NO: 20.

A tumor treatment drug, wherein the drug contains at least any of the foregoing micropeptides HMMW or any of the foregoing nucleotides or the foregoing recombinant vector, and a pharmaceutically acceptable vector.

In an embodiment, the drug is a drug with functions as described in (a1)-(a4), wherein:

(a1) inhibiting tumor growth;

(a2) inhibiting proliferation of tumor cells;

(a3) inhibiting invasion of tumor cells;

(a4) inhibiting migration of tumor cells.

In embodiments, the tumors include head and neck can-cer, thyroid cancer, lung cancer, esophageal squamous cell carcinoma, stomach cancer, breast cancer, kidney cancer and skin cancer.

Compared with the conventional art, embodiments of the present invention have the following advantages:

(1) Embodiments of the present invention provide a micropeptide HMMW with novel amino acid sequences. According to the search of databases (BLAST, UniProt) and literature, no protein or peptide fragments with sequences homologous to micropeptide HMMW were found;

The micropeptide HMMW is composed of 51 amino acids, plays an important role in tumor detection and treat-ment and can be used as a tumor marker for tumors including human head and neck cancer, thyroid cancer, lung cancer, esophageal squamous cell carcinoma, stomach can-cer, breast cancer, kidney cancer and skin cancer, that is, has low expression in the foregoing tumors.

(2) Embodiments of the present invention provide a micropeptide HMMW with novel amino acid sequences. The micropeptide HMMW can significantly inhibit the proliferation, migration and invasion of SCC4 cells of head and neck cancer, SW579 cells of thyroid cancer, A549 cells of lung cancer, TE13 cells of esophageal squamous cell carcinoma, MGC803 cells of stomach cancer, MDA-MB-231 cells of breast cancer, UOK262 cells of kidney cancer, and A431 cells of skin cancer of human in vitro;

The micropeptide HMMW can obviously inhibit the tumor growth of SCC4 cells of head and neck cancer, SW579 cells of thyroid cancer, A549 cells of lung cancer, TE13 cells of esophageal squamous cell carcinoma, MGC803 cells of stomach cancer, MDA-MB-231 cells of breast cancer, UOK262 cells of kidney cancer and A431 cells of skin cancer of human in vivo;

Moreover, micropeptide HMMW can be used as a detec-tion and treatment drug for malignant tumors, thereby greatly expanding the therapeutic spectrum of this micro-peptide and providing a new approach for the development of malignant tumor drugs.

BRIEF DESCRIPTION

Some of the embodiments will be described in detail, with references to the following Figures, wherein like designa-tions denote like members, wherein.

DETAILED DESCRIPTION

The present invention will be further described below in conjunction with specific embodiments.

Embodiment 1

In this embodiment, the encoding ability of HMMW micropeptide was detected.

Figure 1:
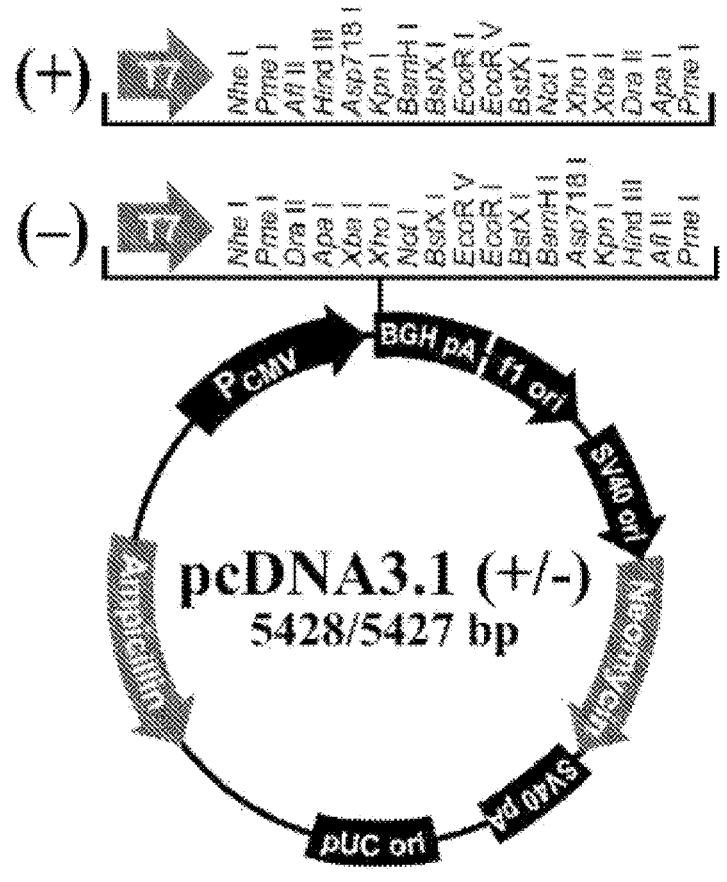
FIG. 1 is a pcDNA3.1 plasmid profile of overexpression micropeptide HMMW in accordance with an embodiment.

Construct in vitro an overexpression vector pcDNA-HMMW with a Flag tag and containing cDNA (its nucleotide sequence is shown in SEQ ID NO: 10), wherein the profile of the empty plasmid pcDNA3.1 is shown in FIG. 1. Introduce the above plasmid into 293T cells by lipo3000 lipofection reagent, collect cells 48 h after transfection, centrifuge, discard the supernatant and collect precipitated cells, rinse the precipitated cells with PBS twice, centrifuge, discard the supernatant and collect the precipitated cells. Add RIPA lysis buffer to the collected precipitated cells, lyse on ice for 20 min, and then centrifuging at 12,000 g for 10 min and collect the supernatant. Then add 1×SDS loading buffer, mix well by pipetting, then boil up and degenerate for 5 min. Separate total protein by 10% SDS-PAGE gel, then transfer it onto a PVDF membrane, block with 5% nonfat dry milk at room temperature for 2 h, incubate with Flag primary antibody (abeam) overnight at 4 DEG C., and wash with TBST 3 times. Incubate with the secondary antibody at room temperature for 1 h and wash with TBST three times. Develop with an ECL supersensitive chemiluminescence solution and use the Tannon imaging system to form images and detect whether there is a target band.

Figure 2:
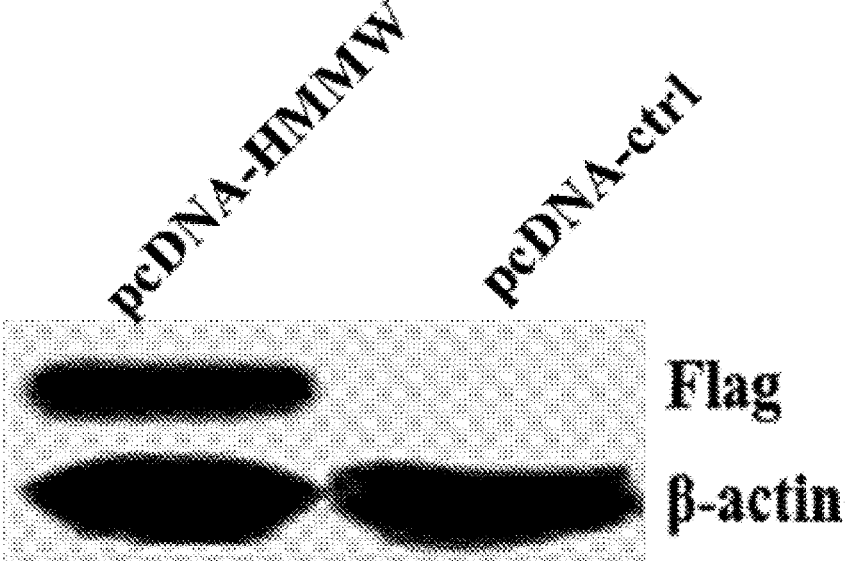
FIG. 2 shows expression of a target band detected by Western blot in accordance with an embodiment.
Figure 3:
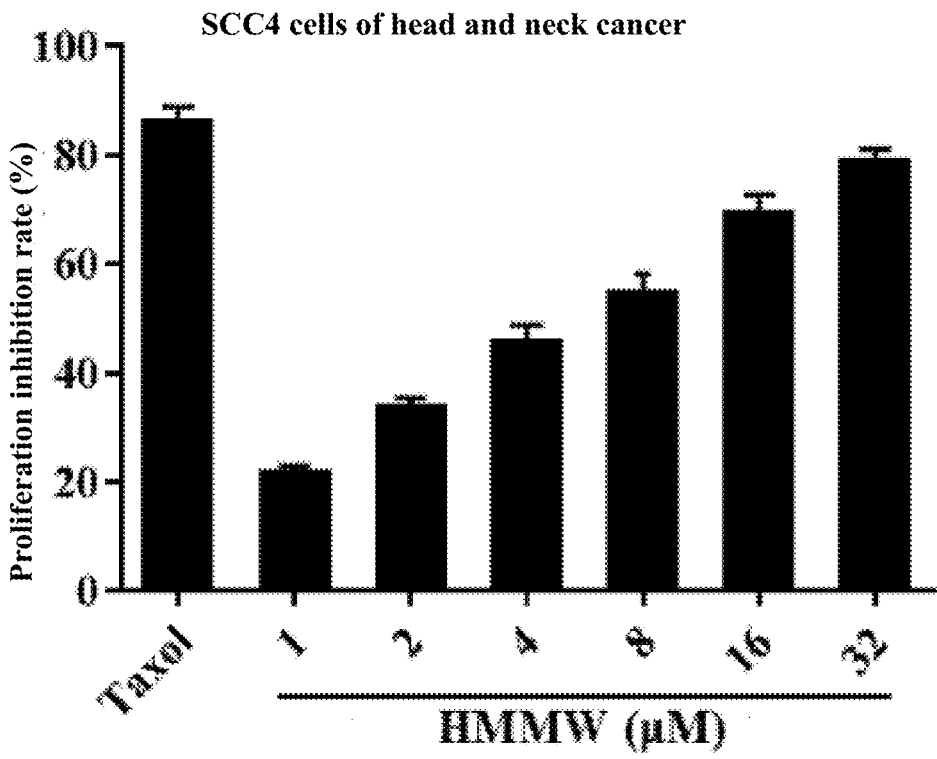
FIG. 3 shows inhibitory effect of micropeptide HMMW on the proliferation of SCC4 cells of human head and neck cancer in accordance with an embodiment.
Figure 4:
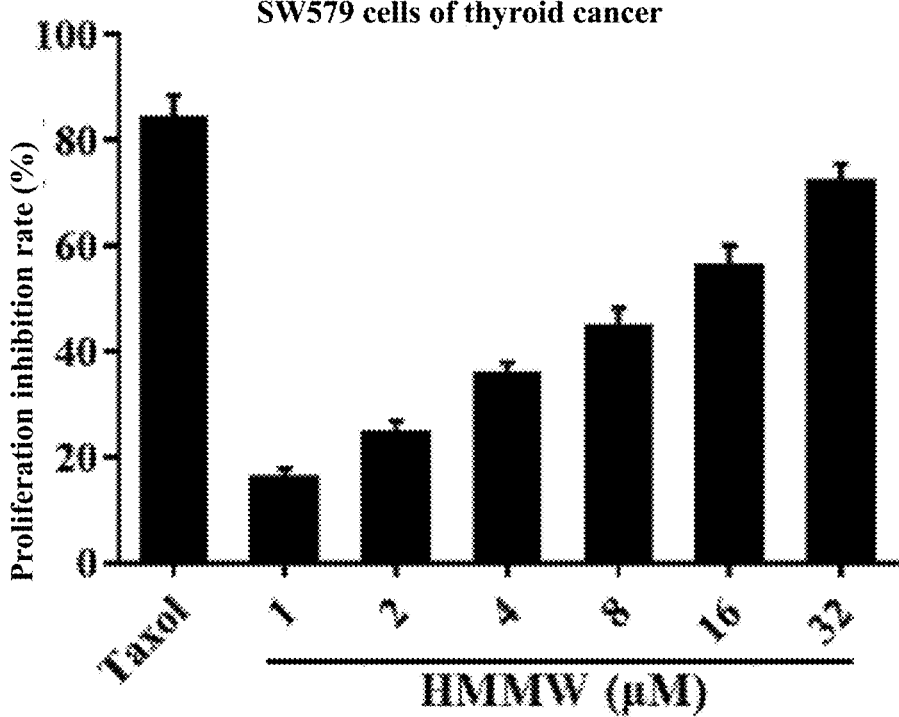
FIG. 4 shows the inhibitory effect of micropeptide HMMW on the proliferation of SW579 cells of human thyroid cancer in accordance with an embodiment.
Figure 5:
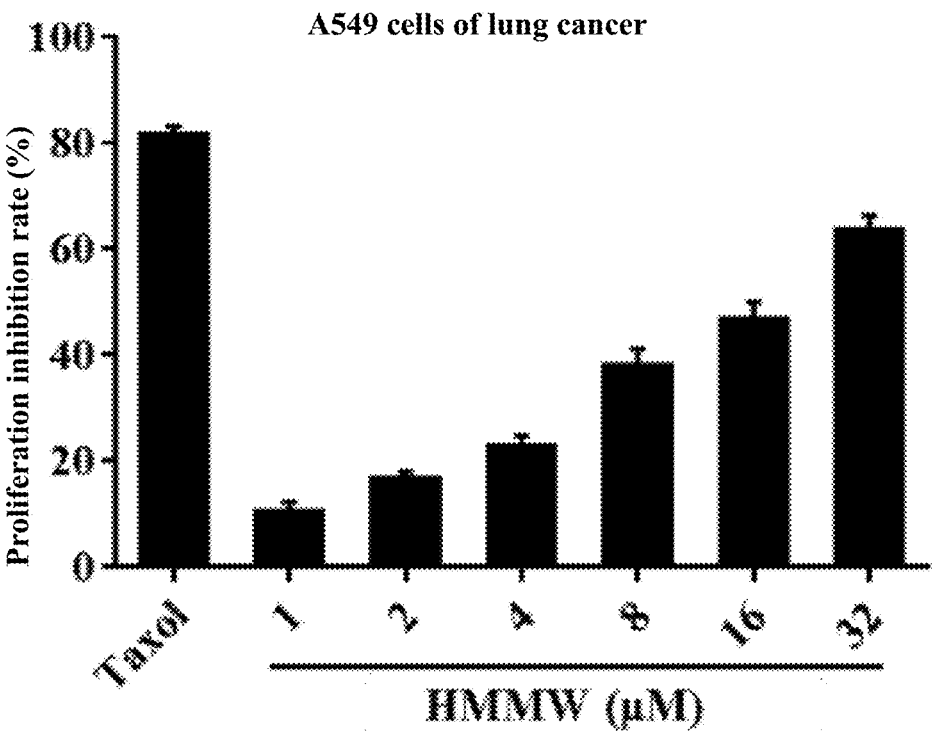
FIG. 5 shows the inhibitory effect of micropeptide HMMW on the proliferation of A549 cells of human lung cancer in accordance with an embodiment.
Figure 6:
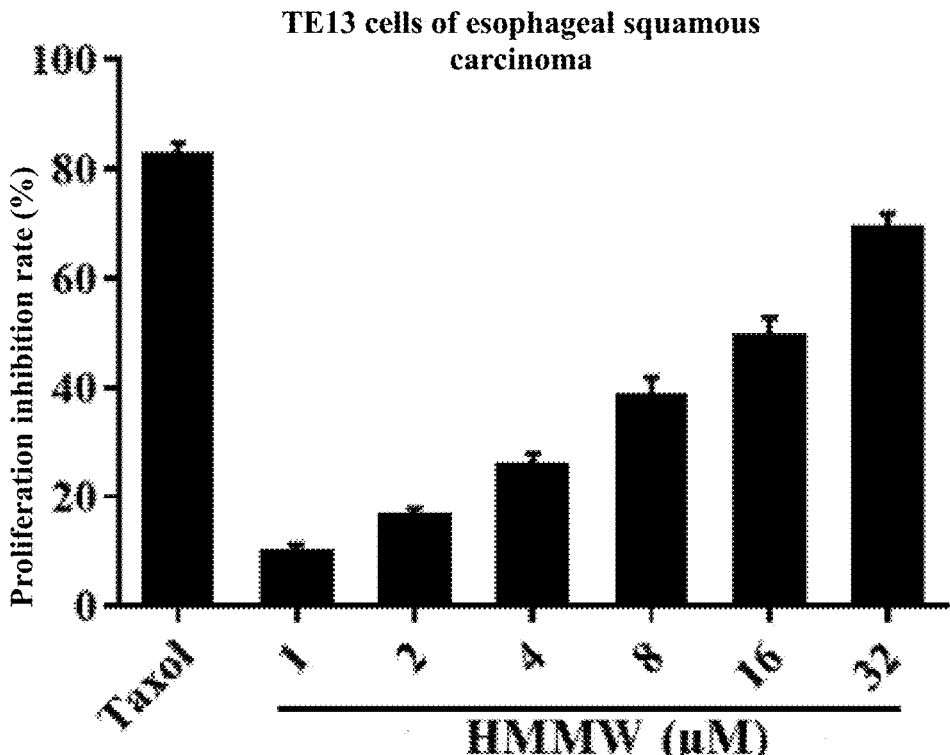
FIG. 6 shows the inhibitory effect of micropeptide HMMW on the proliferation of TE13 cells of esophageal squamous cell carcinoma of human in accordance with an embodiment.
Figure 7:
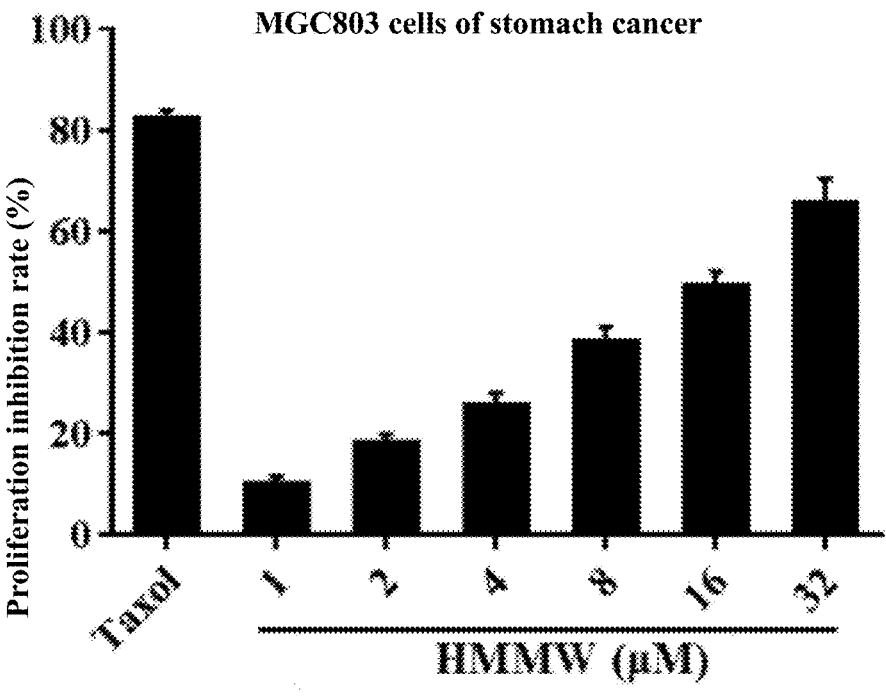
FIG. 7 shows the inhibitory effect of micropeptide HMMW on the proliferation of MGC803 cells of human stomach cancer in accordance with an embodiment.

The results are shown in FIG. 2. It was found through Western blot that a target band of micropeptide HMMW appeared after transfection of the recombinant plasmid. It further indicates that the micropeptide HMMW protein has an encoding ability.

Embodiment 2

In this embodiment, micropeptides HMMW I to IX were obtained by the solid-phase synthesis method and tested.

The micropeptides HMMW Ito IX (their amino acid sequences are shown in SEQ ID NO: 1 to 9) were synthesized by the peptide solid-phase synthesis method, the synthesized micropeptides HMMW were separated and purified by preparative HPLC, and the purity of the micropeptides HMMW was determined by analytical RP-HPLC. In the solid-phase peptide synthesis method, Fmoc-wang-resin or Fmoc-CTC-resin was used as a starting material and then protected amino acids were used to sequentially ligate dipeptide~unpentacontapeptide. After peptide ligation and full wash, peptide cutting and post-treatment were conducted to obtain a crude angiogenesis inhibitor. The crude product was dissolved, purified by preparative HPLC twice, concentrated and freeze-dried to obtain a pure product. Finally, after the tertiary purification, a refined micropeptide product was obtained. This method can not only ensure the efficiency of synthesis, but also raise product purity. The details are as follows:

1. Peptide Ligation (Including Ligation of Dipeptide~Unpentacontapeptide)

Weigh an appropriate amount of Fmoc-wang-resin or Fmoc-CTC-resin, pour it into a glass sand core reaction column, and add an appropriate amount of $CH_2Cl_2$ to fully expand the resin.

a. Removal of protecting group: Add a protecting group removing liquid of hexahydropyridine/N,N-dimethylformamide (DMF), react for a period of time, drain the protecting group removing liquid, wash with DMF once, and add an appropriate amount of the protecting group removing liquid again for reaction to remove Fmoc protecting group;

b. Wash: Drain the protecting group removing liquid, and wash the resin with DMF to thoroughly remove by-products;

c. Condensation: Dissolve the protecting amino acid and activator used for peptide ligation in DMF and condensing agent, shake up, control the temperature at about 34 DEG C., and fully react in the reactor;

d. Wash: Drain the reaction solution and fully wash the resin with DMF to thoroughly remove by-products

2. Peptide Cutting

Put the drained resin into a round-bottom flask, add a cutting fluid to fully lyse hexatriconta-peptide intermediate, and separate the resin from the peptide by a sand core funnel. The components of the cutting fluid and the volume composition of the components are: trifluoroacetic acid:phenol:water:thioanisole:EDT=90:3:3:2:2.

3. Post-Treatment

First add anhydrous ether to the cutting fluid to separate out the peptide, then centrifuge, discard the supernatant, then wash the peptide with anhydrous ether, and drain to obtain a peptide crude product.

4. Purification a. Dissolution: Weigh the crude product to prepare a 5-20 g/L solution, and filter it with a mixed filter membrane with a pore size of 0.45 μm.

Preparation: Conduct primary purification, secondary purification and tertiary purification by semi-preparative HPLC to obtain a qualified refined peptide product. Mobile phase: A is acetonitrile, B is 0.1% TFA aqueous solution.

Primary purification: Equilibrate the preparative column by rinsing with 10%-90% acetonitrile and 20%-80% buffer solution at a flow rate of 50 mL/min-100 mL/min for 10 min. Dissolve the filtered crude product and load it with an infusion pump.

TABLE 1

| Elution gradient for primary purification | | | | |
|---|---|---|---|---|
| Time (min) | Flow rate (mL/min) | A % | B % | Wavelength nm |
| 0 | 60 | 10 | 90 | 220 |
| 40 | 60 | 20 | 80 | 220 |

Collect solutions with an absorption value of greater than 200 mV at UV wavelength 220 nm, combine the solutions with a detected purity of greater than 95% as the peak top, and keep it for secondary separation and purification.

Secondary purification: After removing by rotary evaporation the organic solvent from the peak top received in the primary purification, load the sample by infusion pump in form of 5-95% acetonitrile and 15-85% buffer at a flow rate of 50-100 mL/min.

TABLE 2

| Elution gradient for secondary purification | | | | |
|---|---|---|---|---|
| Time (min) | Flow rate (mL/min) | A % | B % | Wavelength nm |
| 0 | 60 | 5 | 95 | 220 |
| 40 | 60 | 15 | 85 | 220 |

The solutions with absorption greater than 200 mV at UV wavelength 220 nm were collected. The solutions were considered qualified if their purity was greater than 98%.

b. Concentration, filtration and freeze-drying: Concentrate the qualified solution in a rotary evaporator under reduced pressure at 37 DEG C. to remove residual solvent and water for injection. Finally, filter it with a 0.22 μm filter membrane, put the filtrate in a freeze-drying tray and freeze-dry it with a freeze dryer to obtain a pure product.

Tertiary purification: Conduct tertiary purification of the qualified sample with a purification of greater than 98% obtained in the secondary purification, and use 5-95% acetonitrile and 10-90% buffer at a flow rate of 50-100 mL/min to prepare a refined peptide product.

TABLE 3

| Elution gradient for tertiary purification | | | | |
|---|---|---|---|---|
| Time (min) | Flow rate (mL/min) | A % | B % | Wavelength nm |
| 0 | 60 | 5 | 95 | 220 |
| 40 | 60 | 10 | 90 | 220 |

Collect solutions with an absorption value of greater than 200 mV at UV wavelength 220 nm, combine the samples with a detected purity of greater than 95% as the qualified refined product.

5. Purity Detection

Collect freeze-dried purified product and detect peptide purity by analytical RP-HPLC. Analysis conditions: Mobile phase: ACN (+0.1% TFA) and $H_2O$ (+0.1% TFA); linear gradient of acetonitrile: 10%-100%; flow rate: 1 mL/min; operation time: 20 min; loading volume: 20 μL; detection wavelength: 220 nm.

TABLE 4

| Purities of micropeptides HMMW I to IX detected by RP-HPLC | | |
|---|---|---|
| Name | Peak area | Purity (%) |
| HMMW-I | 1349502 | 98.87% |
| HMMW-II | 5510739 | 95.56 |
| HMMW-III | 2578258 | 95.68 |
| HMMW-IV | 8335415 | 98.32 |
| HMMW-V | 2695695 | 95.42 |
| HMMW-VI | 8429617 | 95.19 |
| HMMW-VII | 5562335 | 95.74 |
| HMMW-VIII | 3662672 | 95.66 |
| HMMW-IX | 3293152 | 95.56 |

The purities of synthesized micropeptides were determined by RP-HPLC. The results showed that the purities of the nine prepared micropeptides HMMW were all greater than 95%, which met the design requirements.

In this experiment, micropeptides HMMW I to IX were successfully synthesized by solid-phase synthesis method. This method has high repeatability, strong operability and less pollution; two types of resin, i.e.: wang resin and CTC resin, can be used in the experiment to synthesize peptides; in the experiment, when wang resin was used, it was more stable and had fewer side reactions, a better peak pattern of the process crude product and a higher purification yield compared with other resins, so the cost was lower; in the experiment, when CTC resin was used, the reaction was less affected by temperature and the reaction rate was higher; RP-HPLC was used to purify peptide and gradient elution was used with a better effect compared with isocratic elution. In the separation process, the retention time was appropriate and the production efficiency and the purity were high.

Embodiment 3

In this embodiment, the effects of micropeptides HMMW I to IX on the proliferation ability of human tumor cells were detected.

After SCC4 cells of head and neck cancer, SW579 cells of thyroid cancer, A549 cells of lung cancer, TE13 cells of esophageal squamous cell carcinoma, MGC803 cells of stomach cancer, MDA-MB-231 cells of breast cancer, UOK262 cells of kidney cancer and A431 cells of skin cancer of human were cultured in a 37 DEG C. 5% $CO_2$ incubator until the density was 90%, they were digested and collected by trypsin, the cells were re-suspended in a culture solution and counted under a microscope, the concentration of the cells was adjusted to $3.0 \times 10^4$ cells/mL, and the cell suspension was inoculated to 96-well plates, 100 μL per well, and cultured in a 37 DEG C. 5% $CO_2$ incubator overnight. After the cells were completely adherent, different doses of micropeptides HMMW I to IX were added as drug groups, taxol was used as a positive control group, and the culture solution without any drug was used as a blank control group. They were diluted with the culture solution till predetermined concentrations. The diluted solutions were added to 96-well plates, respectively, 100 µL per well, and incubated in a 37 DEG C. 5% $CO_2$ incubator for 48 h. 20 µL of 5 mg/mL MTT was added to each well of the 96-well plates, and the culture was continued for 4 h. The culture medium was sucked away, and 100 µL of DMSO was added to each well for dissolution. Absorbance was detected by ELIASA at detection wavelength 570 nm and reference wavelength 630 nm, and proliferation inhibition (PI) was calculated according to Formula PI (%)=1−drug group/ negative group. The test was independently repeated three times. The results obtained from the test were expressed with mean±SD and statistical t test was done. *P<0.05 means significant difference, and **P<0.01 means very significant difference.

The results are shown in FIG. 3 to FIG. 10. Compared with the negative control group, micropeptide HMMW-I at a dose of 1 to 32 µM could significantly inhibit the proliferation of SCC4 cells of head and neck cancer (FIG. 3), SW579 cells of thyroid cancer (FIG. 4), A549 cells of lung cancer (FIG. 5), TE13 cells of esophageal squamous cell carcinoma (FIG. 6), MGC803 cells of stomach cancer (FIG. 7), MDA-MB-231 cells of breast cancer (FIG. 8), UOK262 cells of kidney cancer (FIG. 9), A431 cells of skin cancer (FIG. 10) of human to various extent, and showed a dose-dependent relation. The results are shown in Table 5. Compared with the negative control, micropeptides HMMW I to IX at a dose of 1 to 32 µM all could significantly inhibit the proliferation of SCC4 cells of head and neck cancer, SW579

TABLE 5

Inhibitory effects of micropeptides HMMW I to IX on proliferation of human tumor cells

| Group | Dose (µM) | Tumor type (inhibition rate/%) | | | | | | | |
|---|---|---|---|---|---|---|---|---|---|
| | | SCC4 | SW579 | A549 | TE13 | MGC803 | MDA-MB-231 | UOK262 | A431 |
| HMMW-I | 1 | 20.18 | 18.98 | 14.71 | 13.09 | 15.93 | 18.90 | 16.92 | 17.04 |
| | 2 | 32.67 | 24.87 | 19.37 | 17.27 | 19.91 | 23.17 | 24.15 | 20.98 |
| | 4 | 44.89 | 36.23 | 21.87 | 23.98 | 24.09 | 36.99 | 38.19 | 31.09 |
| | 8 | 58.19 | 42.17 | 37.09 | 36.09 | 38.18 | 45.06 | 43.54 | 41.21 |
| | 16 | 64.29 | 59.02 | 43.92 | 43.53 | 45.10 | 56.19 | 59.21 | 48.02 |
| | 32 | 79.18 | 68.01 | 58.90 | 61.02 | 68.09 | 69.18 | 72.10 | 65.09 |
| HMMW-II | 1 | 19.58 | 17.90 | 14.09 | 12.45 | 16.23 | 17.38 | 16.23 | 16.44 |
| | 2 | 31.62 | 26.81 | 18.21 | 16.89 | 18.57 | 22.45 | 23.32 | 22.18 |
| | 4 | 42.34 | 33.19 | 22.45 | 22.68 | 23.18 | 35.57 | 34.29 | 30.29 |
| | 8 | 55.41 | 41.57 | 35.05 | 35.16 | 39.16 | 46.48 | 42.34 | 40.41 |
| | 16 | 60.15 | 54.15 | 42.54 | 44.37 | 44.15 | 55.24 | 52.51 | 45.32 |
| | 32 | 72.14 | 63.25 | 56.87 | 60.13 | 63.24 | 61.35 | 70.70 | 62.19 |
| HMMW-III | 1 | 17.18 | 17.91 | 15.73 | 14.04 | 16.90 | 16.94 | 17.90 | 18.34 |
| | 2 | 30.67 | 23.80 | 18.34 | 18.21 | 18.95 | 22.12 | 23.15 | 23.58 |
| | 4 | 41.89 | 35.21 | 23.85 | 20.90 | 25.01 | 35.91 | 35.16 | 34.03 |
| | 8 | 53.19 | 41.12 | 35.01 | 34.03 | 39.13 | 44.05 | 41.53 | 42.11 |
| | 16 | 60.29 | 55.00 | 41.90 | 44.50 | 47.16 | 52.14 | 57.20 | 49.06 |
| | 32 | 73.18 | 64.00 | 54.84 | 60.09 | 65.05 | 67.13 | 70.16 | 67.19 |
| HMMW-IV | 1 | 17.54 | 18.94 | 15.06 | 14.43 | 15.20 | 16.34 | 17.23 | 15.43 |
| | 2 | 30.32 | 27.21 | 19.23 | 17.59 | 19.37 | 23.25 | 24.12 | 23.28 |
| | 4 | 41.31 | 35.39 | 24.41 | 23.62 | 24.15 | 36.53 | 36.25 | 34.25 |
| | 8 | 53.21 | 40.51 | 36.35 | 32.46 | 37.36 | 47.28 | 43.24 | 42.31 |
| | 16 | 62.13 | 52.05 | 41.50 | 43.31 | 45.12 | 53.21 | 54.31 | 48.30 |
| | 32 | 70.34 | 61.21 | 54.27 | 58.33 | 61.54 | 60.25 | 69.75 | 60.29 |
| HMMW-V | 1 | 16.13 | 16.51 | 16.76 | 15.07 | 15.93 | 17.92 | 18.95 | 17.35 |
| | 2 | 32.27 | 22.86 | 19.14 | 19.11 | 19.92 | 21.32 | 21.35 | 22.38 |
| | 4 | 40.84 | 34.11 | 22.80 | 22.94 | 24.05 | 33.95 | 33.11 | 31.05 |
| | 8 | 52.09 | 40.10 | 36.31 | 32.53 | 38.11 | 42.35 | 40.43 | 40.31 |
| | 16 | 61.24 | 54.40 | 42.95 | 41.57 | 46.36 | 50.12 | 55.24 | 47.05 |
| | 32 | 70.28 | 63.05 | 55.54 | 59.39 | 63.00 | 64.33 | 67.26 | 65.39 |
| HMMW-VI | 1 | 15.41 | 17.58 | 16.01 | 15.83 | 16.10 | 15.54 | 18.53 | 14.43 |
| | 2 | 32.18 | 25.20 | 18.13 | 18.49 | 18.27 | 22.22 | 25.15 | 22.21 |
| | 4 | 40.21 | 33.35 | 23.40 | 22.32 | 23.13 | 34.33 | 33.15 | 33.35 |
| | 8 | 52.20 | 41.50 | 34.30 | 31.44 | 36.26 | 45.24 | 41.20 | 40.30 |
| | 16 | 60.03 | 50.45 | 40.54 | 42.51 | 44.10 | 51.31 | 53.11 | 46.20 |
| | 32 | 68.14 | 60.20 | 52.23 | 54.30 | 60.34 | 62.27 | 64.73 | 58.24 |
| HMMW-VII | 1 | 15.33 | 15.53 | 15.86 | 16.17 | 15.93 | 18.52 | 19.45 | 16.25 |
| | 2 | 31.21 | 21.56 | 18.13 | 18.18 | 19.92 | 20.12 | 20.31 | 21.35 |
| | 4 | 41.54 | 33.14 | 22.60 | 21.54 | 24.05 | 32.45 | 32.21 | 30.15 |
| | 8 | 51.02 | 41.00 | 35.30 | 33.50 | 38.11 | 41.15 | 41.40 | 39.30 |
| | 16 | 63.14 | 52.45 | 43.75 | 40.47 | 46.36 | 52.02 | 52.14 | 44.25 |
| | 32 | 71.20 | 61.15 | 53.51 | 57.33 | 63.00 | 63.23 | 64.25 | 64.32 |
| HMMW-VIII | 1 | 16.18 | 16.91 | 13.73 | 15.04 | 15.90 | 17.94 | 18.90 | 16.34 |
| | 2 | 31.67 | 22.80 | 17.34 | 19.21 | 19.95 | 21.12 | 22.15 | 22.58 |
| | 4 | 40.89 | 32.21 | 21.85 | 21.90 | 23.01 | 34.91 | 33.16 | 33.03 |
| | 8 | 51.19 | 40.12 | 32.01 | 33.03 | 35.13 | 43.05 | 40.53 | 41.11 |
| | 16 | 61.29 | 52.00 | 40.90 | 42.50 | 46.16 | 50.14 | 54.20 | 48.06 |
| | 32 | 70.18 | 60.00 | 53.84 | 61.09 | 63.05 | 64.13 | 71.16 | 66.19 |
| HMMW-IX | 1 | 16.33 | 16.53 | 16.86 | 17.17 | 18.93 | 19.52 | 18.45 | 18.25 |
| | 2 | 33.21 | 22.56 | 19.13 | 19.18 | 21.92 | 23.12 | 22.31 | 23.35 |
| | 4 | 42.54 | 31.14 | 23.60 | 22.54 | 25.05 | 34.45 | 33.21 | 31.15 |
| | 8 | 50.02 | 45.00 | 36.30 | 35.50 | 39.11 | 42.15 | 43.40 | 39.30 |
| | 16 | 64.14 | 54.45 | 45.75 | 43.47 | 47.36 | 53.02 | 54.14 | 43.25 |
| | 32 | 72.20 | 63.15 | 54.51 | 58.33 | 64.00 | 62.23 | 65.25 | 61.32 |
| Taxol | 10 (µg/ml) | 87.02 | 82.83 | 84.29 | 79.21 | 81.28 | 83.92 | 83.92 | 85.19 |

11 12 cells of thyroid cancer, A549 cells of lung cancer, TE13 cells of esophageal squamous cell carcinoma, MGC803 cells of stomach cancer, MDA-MB-231 cells of breast cancer, UOK262 cells of kidney cancer, A431 cells of skin cancer of human, and showed a dose-dependent relation. It indicates that the peptides with more than 85% homology to the original sequence HMMW I all have an inhibitory effect on the proliferation of tumor cells, and it can be considered to use micropeptides HMMW I to IX as candidate anti-tumor drugs.

Embodiment 4

Effects of Micropeptides HMMW I to IX on the Migration Ability of Human Tumor Cells Inoculate SCC4 cells of head and neck cancer, SW579 cells of thyroid cancer, A549 cells of lung cancer, TE13 cells of esophageal squamous cell carcinoma, MGC803 cells of stomach cancer, MDA-MB-231 cells of breast cancer, UOK262 cells of kidney cancer, and A431 cells of skin $$MIR(\%) = 1 - \frac{N_{test}}{N_{control}} \times 100\%$$

where $N_{test}$ is the number of migrated cells in the test groups (the groups at a dose of 1, 4 or 14 μM in the table), $N_{control}$ is the number of migrated cells in the blank control groups (the groups at a dose of 0 μM in the table).

The test was repeated independently three times. Mean±SD was calculated based on the test results. Statistical t test was done. Here, "the test was repeated independently three times" means that every dose of any type of cells was tested repeatedly three times, and then the above formula was used to calculate the number of migrated cells (Mean±SD). Value P was used to express statistical difference. The statistical significance of the results is a method for estimating how true the results are (the totality can be represented), *P<0.05 means significant difference, and **P<0.01 means very significant difference.

TABLE 6

Inhibitory effects of micropeptides HMMW I to IX on the migration ability of human tumor cells

| Group | Dose (μM) | SCC4 | SW579 | A549 | TE13 | MGC803 | MDA-MB-231 | UOK262 | A431 |
|---|---|---|---|---|---|---|---|---|---|
| HMMW-I | 1 | 17.85% | 19.81% | 35.00% | 23.76% | 27.61% | 28.06% | 15.39% | 33.19% |
| | 4 | 42.97% | 51.03% | 53.95% | 42.29% | 53.45% | 50.34% | 42.38% | 55.17% |
| | 16 | 77.00% | 70.98% | 73.46% | 68.32% | 76.80% | 75.38% | 71.47% | 73.22% |
| HMMW-II | 1 | 18.81% | 18.80% | 34.01% | 22.74% | 25.64% | 27.07% | 16.29% | 31.14% |
| | 4 | 43.67% | 50.13% | 52.91% | 40.23% | 52.41% | 51.24% | 41.28% | 53.12% |
| | 16 | 75.04% | 71.92% | 72.36% | 65.31% | 73.82% | 73.18% | 70.43% | 71.12% |
| HMMW-III | 1 | 16.81% | 18.83% | 33.01% | 22.76% | 25.61% | 27.06% | 16.39% | 32.13% |
| | 4 | 43.94% | 50.04% | 54.93% | 41.29% | 52.45% | 51.34% | 41.38% | 54.27% |
| | 16 | 74.01% | 71.92% | 72.42% | 65.32% | 74.80% | 74.38% | 70.47% | 72.21% |
| HMMW-IV | 1 | 16.84% | 18.81% | 33.00% | 22.76% | 25.60% | 29.06% | 16.32% | 32.19% |
| | 4 | 43.91% | 50.03% | 52.91% | 41.29% | 52.45% | 51.34% | 41.38% | 54.17% |
| | 16 | 75.04% | 71.91% | 71.46% | 65.32% | 74.80% | 73.38% | 70.47% | 71.24% |
| HMMW-V | 1 | 18.36% | 17.45% | 35.01% | 23.74% | 27.64% | 28.07% | 18.29% | 30.14% |
| | 4 | 44.67% | 51.13% | 53.91% | 42.23% | 54.41% | 50.24% | 42.28% | 54.12% |
| | 16 | 71.04% | 71.93% | 71.36% | 64.31% | 75.82% | 74.18% | 72.43% | 70.12% |
| HMMW-VI | 1 | 16.69% | 19.81% | 32.00% | 21.76% | 26.64% | 27.06% | 17.32% | 33.19% |
| | 4 | 42.81% | 52.03% | 51.90% | 40.21% | 51.45% | 50.34% | 40.38% | 55.17% |
| | 16 | 71.04% | 70.91% | 70.46% | 66.32% | 72.80% | 74.38% | 72.47% | 70.23% |
| HMMW-VII | 1 | 17.42% | 20.80% | 35.01% | 23.64% | 26.60% | 28.27% | 19.24% | 32.10% |
| | 4 | 44.61% | 53.13% | 53.91% | 41.21% | 51.31% | 50.14% | 40.21% | 52.22% |
| | 16 | 72.34% | 70.92% | 71.36% | 63.30% | 70.62% | 72.15% | 72.40% | 70.11% |
| HMMW-VIII | 1 | 17.80% | 18.81% | 32.06% | 23.73% | 24.60% | 26.14% | 18.29% | 33.10% |
| | 4 | 42.92% | 52.05% | 51.90% | 42.23% | 53.43% | 50.24% | 43.48% | 53.37% |
| | 16 | 72.35% | 70.90% | 73.40% | 63.31% | 73.81% | 73.32% | 71.45% | 71.20% |
| HMMW-IX | 1 | 18.81% | 17.81% | 36.00% | 21.76% | 25.61% | 26.06% | 17.39% | 33.19% |
| | 4 | 43.97% | 50.03% | 52.95% | 40.29% | 51.45% | 52.34% | 43.38% | 55.17% |
| | 16 | 74.00% | 71.98% | 71.46% | 65.32% | 74.80% | 73.38% | 70.47% | 73.22% |
| Avastin | 10 | 68.64% | 59.81% | 66.21% | 58.19% | 71.25% | 62.19% | 61.39% | 64.63% | cancer of human to transwell cells, 100 μL per well, and meanwhile add micropeptides HMMW I to IX at different doses to every cell. Add 0.6 mL of complete medium containing 10% FBS to the transwell cells to stimulate cell migration, and culture in 5% $CO_2$ at 37 DEG C. for 24 h. Discard the medium in the wells, fix with 90% alcohol at room temperature for 30 min, stain with 0.1% crystal violet at room temperature for 10 min, rinse with clear water, gently wipe off the non-migrated cells in the upper layer with a cotton swab, observe under a microscope and select four fields of view to take pictures and count. Calculate the migration inhibition rate (MIR) of the cells according to the following formula:

The results are shown in Table 6. Compared with the negative control group, micropeptides HMMW I to IX at a dose of 1 to 16 μM all could significantly inhibit the migration of SCC4 cells of head and neck cancer, SW579 cells of thyroid cancer, A549 cells of lung cancer, TE13 cells of esophageal squamous cell carcinoma, MGC803 cells of stomach cancer, MDA-MB-231 cells of breast cancer, UOK262 cells of kidney cancer, A431 cells of skin cancer of human to various extent, and showed a dose-dependent relation. It indicates that the peptides with more than 85% homology to the original sequence HMMW I all have an inhibitory effect on the migration of tumor cells and can be used as treatment drugs to inhibit the migration ability of malignant tumor cells.

13

Embodiment 5

Effects of Micropeptides HMMW I to IX on the Invasion Ability of Human Tumor Cells Dilute 10 mg/mL Matrigel with culture medium at 1:3, spread it on membranes of transwell cells and dry it in the air at room temperature. Use trypsin to digest and collect SCC4 cells of head and neck cancer, SW579 cells of thyroid cancer, A549 cells of lung cancer, TE13 cells of esophageal

14 is the number of invaded cells in the blank control groups (the groups at a dose of 0 µM in the table). The test was repeated independently three times. Mean±SD was calculated based on the test results. Statistical t test was done. Value P was used to express statistical difference. The statistical significance of the results is a method for estimating how true the results are (the totality can be represented), *P<0.05 means significant difference, and **P<0.01 means very significant difference.

TABLE 7

| | | Tumor type (inhibition rate) | | | | | | | |
|---|---|---|---|---|---|---|---|---|---|
| Group | Dose | SCC4 | SW579 | A549 | TE13 | MGC803 | MDA-MB-231 | UOK262 | A431 |
| HMMW-I | 1 | 20.75% | 19.63% | 31.23% | 20.43% | 26.12% | 27.97% | 33.80% | 32.74% |
| | 4 | 46.24% | 44.76% | 51.32% | 42.86% | 50.08% | 48.95% | 53.12% | 51.22% |
| | 16 | 74.84% | 64.89% | 64.08% | 66.51% | 68.62% | 70.49% | 66.67% | 69.37% |
| HMMW-II | 1 | 21.72% | 22.13% | 33.25% | 21.41% | 27.52% | 25.93% | 34.70% | 31.71% |
| | 4 | 45.14% | 45.78% | 55.12% | 43.46% | 51.04% | 47.75% | 54.16% | 53.41% |
| | 16 | 73.80% | 66.73% | 65.09% | 64.56% | 66.51% | 71.52% | 65.64% | 68.25% |
| HMMW-III | 1 | 22.75% | 18.63% | 32.13% | 21.23% | 25.11% | 28.91% | 34.37% | 33.70% |
| | 4 | 48.24% | 42.76% | 52.30% | 41.81% | 53.38% | 49.82% | 55.15% | 53.21% |
| | 16 | 75.84% | 63.89% | 66.09% | 63.31% | 67.61% | 68.36% | 67.23% | 67.33% |
| HMMW-IV | 1 | 22.79% | 23.10% | 34.22% | 22.40% | 23.50% | 24.91% | 38.40% | 36.25% |
| | 4 | 47.34% | 46.71% | 56.11% | 42.42% | 54.21% | 46.73% | 58.36% | 57.19% |
| | 16 | 74.40% | 67.72% | 65.24% | 67.51% | 63.49% | 71.64% | 67.62% | 71.36% |
| HMMW-V | 1 | 20.34% | 19.09% | 31.19% | 20.29% | 26.53% | 27.25% | 33.43% | 32.19% |
| | 4 | 46.26% | 44.23% | 51.27% | 42.74% | 50.24% | 48.37% | 53.27% | 51.35% |
| | 16 | 74.71% | 64.14% | 64.25% | 66.69% | 68.38% | 70.50% | 66.14% | 69.29% |
| HMMW-VI | 1 | 22.83% | 23.29% | 34.15% | 22.25% | 23.42% | 24.83% | 38.15% | 36.83% |
| | 4 | 47.82% | 46.63% | 56.32% | 42.39% | 54.19% | 46.57% | 58.28% | 57.35% |
| | 16 | 74.16% | 67.58% | 65.35% | 67.47% | 63.35% | 71.43% | 67.51% | 71.16% |
| HMMW-VII | 1 | 19.70% | 20.11% | 32.22% | 25.11% | 29.50% | 27.91% | 36.74% | 34.70% |
| | 4 | 43.11% | 43.72% | 52.42% | 45.36% | 54.34% | 49.55% | 56.26% | 55.51% |
| | 16 | 70.84% | 63.71% | 64.02% | 67.52% | 69.57% | 74.32% | 67.62% | 69.24% |
| HMMW-VIII | 1 | 23.71% | 19.61% | 34.03% | 24.21% | 26.01% | 27.90% | 35.27% | 34.50% |
| | 4 | 49.14% | 43.56% | 55.20% | 42.31% | 57.18% | 45.81% | 54.14% | 55.11% |
| | 16 | 76.64% | 64.79% | 68.03% | 61.51% | 70.60% | 64.26% | 68.21% | 69.43% |
| HMMW-IX | 1 | 24.83% | 25.21% | 30.15% | 21.25% | 26.42% | 27.83% | 39.15% | 34.83% |
| | 4 | 48.82% | 48.60% | 60.32% | 40.39% | 57.19% | 49.57% | 59.28% | 54.35% |
| | 16 | 75.16% | 62.48% | 70.35% | 65.47% | 68.35% | 75.43% | 69.51% | 74.16% |
| Avastin | 10 | 68.41% | 67.40% | 61.35% | 69.31% | 63.48% | 70.03% | 72.16% | 70.39% |

Inhibitory effects of micropeptides HMMW I to IX on the invasion ability of human tumor cells squamous cell carcinoma, MGC803 cells of stomach cancer, MDA-MB-231 cells of breast cancer, UOK262 cells of kidney cancer, and A431 cells of skin cancer of human, which were cultured to the logarithmic phase, wash with PBS twice and re-suspend with a blank culture medium. Adjust cell concentration to $1 \times 10^5$ cells/mL. Inoculate the cells to transwell cells, 100 µL per well, and meanwhile add micropeptides HMMW I to IX at different doses to every cell. Add 0.6 mL of complete medium containing 10% FBS to the transwell cells to stimulate cell invasion, and culture in 5% $CO_2$ at 37 DEG C. for 24 h. Discard the medium in the wells, fix with 90% alcohol at room temperature for 30 min, stain with 0.1% crystal violet at room temperature for 10 min, rinse with clear water, gently wipe off the non-invaded cells in the upper layer with a cotton swab, observe under a microscope and select four fields of view to take pictures and count. Calculate the invasion inhibition rate (IIR) of the cells according to the following formula:

$$IIR(\%) = 1 - \frac{N_{test}}{N_{control}} \times 100\%$$

where $N_{test}$ is the number of invaded cells in the test groups (the groups at a dose of 1, 4 or 16 µM in the table), $N_{control}$ The results are shown in Table 7. Micropeptides HMMW I to IX all can significantly inhibit the migration of SCC4 cells of head and neck cancer, SW579 cells of thyroid cancer, A549 cells of lung cancer, TE13 cells of esophageal squamous cell carcinoma, MGC803 cells of stomach cancer, MDA-MB-231 cells of breast cancer, UOK262 cells of kidney cancer, A431 cells of skin cancer of human to various extent, and showed a dose-dependent relation. It indicates that the peptides with more than 85% homology to the original sequence HMMW I all have an inhibitory effect on the invasion of tumor cells and can be used as treatment drugs to inhibit the invasion ability of malignant tumor cells.

Embodiment 6

Effects of Micropeptide HMMW on In Vivo Growth of Human Tumor Cells (1) Massively culture SCC4 cells of head and neck cancer, SW579 cells of thyroid cancer, A549 cells of lung cancer, TE13 cells of esophageal squamous cell carcinoma, MGC803 cells of stomach cancer, MDA-MB-231 cells of breast cancer, UOK262 cells of kidney cancer, and A431 cells of skin cancer of human, digest with a 0.25% pancreatin solution, centrifuge the cell suspension at 1,000 rpm for 5 min after termination of digestion, re-suspend the cells by serum-free DMEM culture medium, then count the cells and adjust cell concentration to $5\times10^7$ cells/ml;

(2) Inoculate each nude mouse (female mice at the age of 4-6 weeks and with a weight of 14-16 g were ordered and adaptively reared for 1 week in an SPF animal breeding room) with 100 µl of the cell suspension of the corresponding group in the left armpit, and the number of cells injected is $5\times10^6$;

(3) After inoculation, the tumor growth at the inoculation sites of nude mice was closely observed. On the $7^{th}$ day after inoculation, white scabs appeared at the inoculation sites, which could move subcutaneously after being touched. With the growth of tumor tissue, hard tumor masses were gradually formed at the inoculation sites. On about the $14^{th}$ day, the average volume of the tumor tissue reached 100 mm$^3$. BALB/c nude mice were randomly divided into three groups (the normal saline group was a blank control group, the micropeptide HMMW at a dose of 10 mg/kg was a low-dose group, and the micropeptide HMMW at a dose of 15 mg/kg was a high-dose group), 6 mice in each group, and the animals weighed 16-18 g at the beginning of administration;

(4) The volume of the transplanted tumor was measured and recorded every two days. The calculation formula of tumor volume (TV) is shown below:

$$TV = 0.5 \times a \times b^2$$

where, a is the length of the transplanted tumor (mm), and b is the width of the transplanted tumor (mm).

The results are shown in FIG. 11 to FIG. 18. Compared with the normal saline control group, micropeptide HMMW could significantly inhibit the tumorigenicity in vivo of SCC4 cells of head and neck cancer (FIG. 11), SW579 cells of thyroid cancer (FIG. 12), A549 cells of lung cancer (FIG.

cancer, TE13 cells of esophageal squamous cell carcinoma, MGC803 cells of stomach cancer, MDA-MB-231 cells of breast cancer, UOK262 cells of kidney cancer, and A431 cells of skin cancer of human, digest with a 0.25% pancreatin solution, centrifuge the cell suspension at 1,000 rpm for 5 min after termination of digestion, re-suspend the cells by serum-free DMEM culture medium, then count the cells and adjust cell concentration to $5\times10^7$ cells/ml;

(2) Inoculate each nude mouse (female mice at the age of 4-6 weeks and with a weight of 14-16 g were ordered and adaptively reared for 1 week in an SPF animal breeding room) with 100 µl of the cell suspension of the corresponding group in the left armpit, and the number of cells injected is $5\times10^6$;

(3) After inoculation, the tumor growth at the inoculation sites of nude mice was closely observed. On the $7^{th}$ day after inoculation, white scabs appeared at the inoculation sites, which could move subcutaneously after being touched. With the growth of tumor tissue, hard tumor masses were gradually formed at the inoculation sites. On about the $14^{th}$ day, the average volume of the tumor tissue reached 100 mm$^3$. BALB/c nude mice were randomly divided into three groups (the normal saline group was a blank control group, and each of micropeptides HMMW I to IX formed a group at a dose of 15 mg/kg), 6 mice in each group, and the animals weighed 16-18 g at the beginning of administration;

(4) The volume of the transplanted tumor was measured and recorded every two days. The calculation formula of tumor volume (TV) is shown below:

$$TV = 0.5 \times a \times b^2$$

where, a is the length of the transplanted tumor (mm), and b is the width of the transplanted tumor (mm).

TABLE 8

Inhibitory effects of micropeptides HMMW I to IX on in vivo tumor growth of human tumor cells

| Group (n = 6) | Tumor type (inhibition rate) | | | | | | | |
|---|---|---|---|---|---|---|---|---|
| | SCC4 | SW579 | A549 | TE13 | MGC803 | MDA-MB-231 | UOK262 | A431 |
| HMMW-I | 72.56% | 66.63% | 69.23% | 65.43% | 68.12% | 67.97% | 63.80% | 62.74% |
| HMMW-II | 66.24% | 64.76% | 71.32% | 62.86% | 70.08% | 68.95% | 63.12% | 71.22% |
| HMMW-III | 70.84% | 71.89% | 73.08% | 66.31% | 69.62% | 69.49% | 61.67% | 69.54% |
| HMMW-IV | 71.72% | 72.13% | 68.25% | 61.41% | 67.52% | 65.93% | 64.70% | 71.71% |
| HMMW-V | 67.14% | 70.78% | 71.12% | 63.46% | 71.04% | 67.75% | 64.16% | 69.41% |
| HMMW-VI | 73.54% | 66.79% | 65.27% | 65.56% | 66.51% | 71.18% | 65.19% | 68.25% |
| HMMW-VII | 72.75% | 68.63% | 69.13% | 71.23% | 65.11% | 68.91% | 64.37% | 67.70% |
| HMMW-VIII | 68.24% | 71.76% | 69.30% | 68.81% | 69.38% | 69.82% | 65.15% | 68.21% |
| HMMW-IX | 71.84% | 67.89% | 69.09% | 65.31% | 68.61% | 69.36% | 65.23% | 64.33% |

13), TE13 cells of esophageal squamous cell carcinoma (FIG. 14), MGC803 cells of stomach cancer (FIG. 15), MDA-MB-231 cells of breast cancer (FIG. 16), UOK262 cells of kidney cancer (FIG. 17), A431 cells of skin cancer (FIG. 18) of human to various extent and showed a dose-dependent relation, so it can be considered to use micropeptide HMMW as a new type of antitumor peptide.

Embodiment 7

Figure 8:
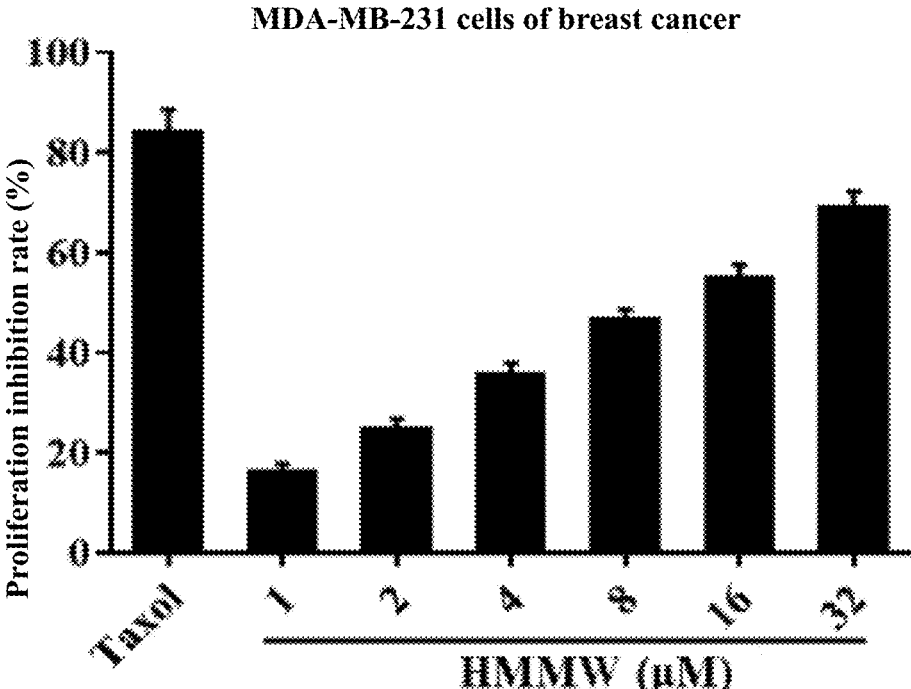
FIG. 8 shows the inhibitory effect of micropeptide HMMW on the proliferation of MDA-MB-231 cells of human breast cancer in accordance with an embodiment.
Figure 9:
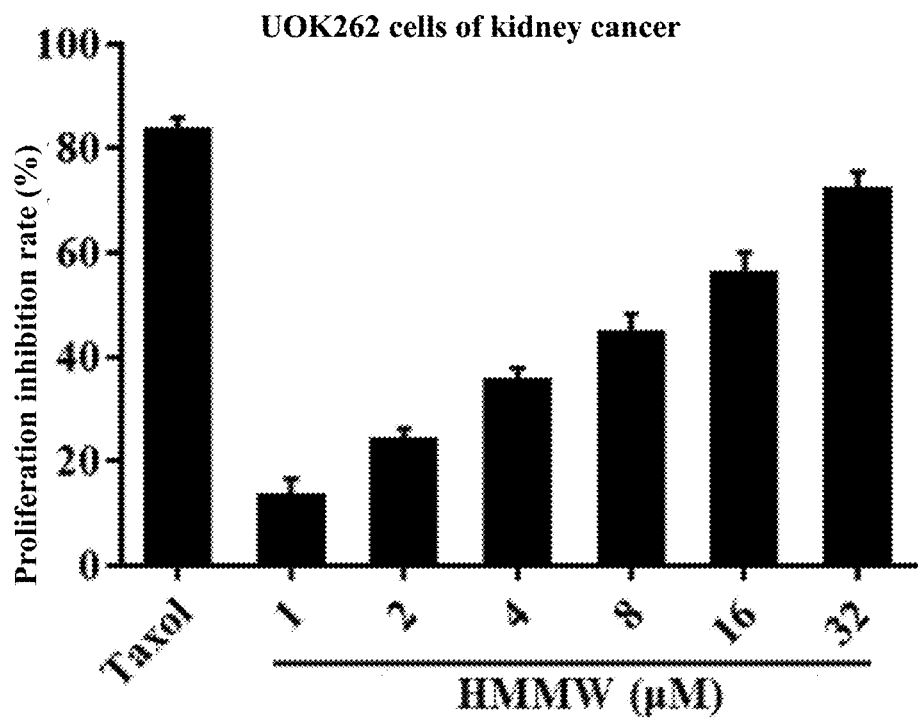
FIG. 9 shows the inhibitory effect of micropeptide HMMW on the proliferation of UOK262 cells of human kidney cancer in accordance with an embodiment.
Figure 10:
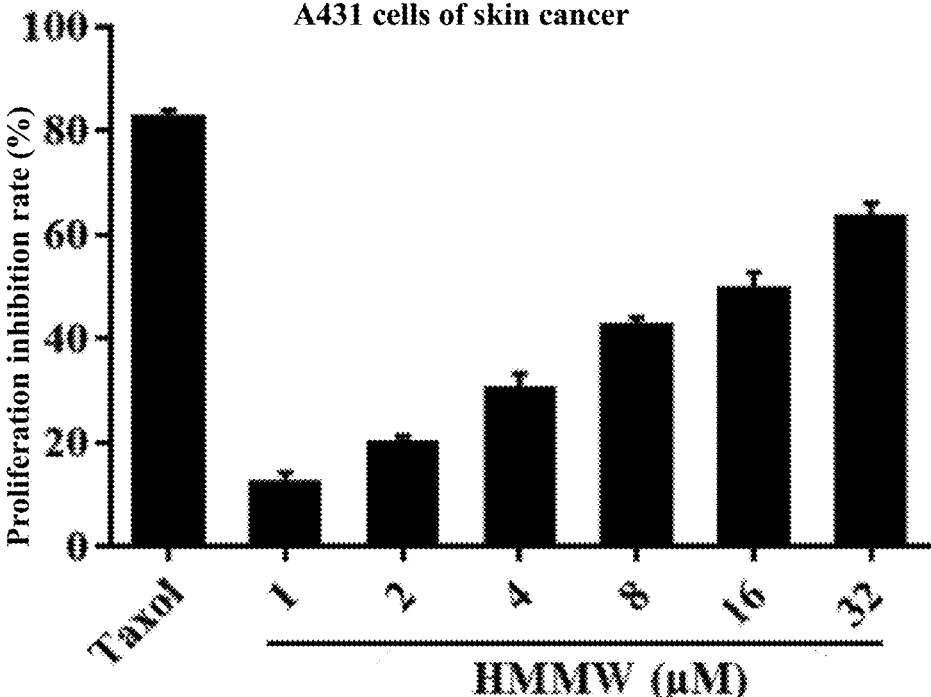
FIG. 10 shows the inhibitory effect of micropeptide HMMW on the proliferation of A431 cells of human skin cancer in accordance with an embodiment.
Figure 11:
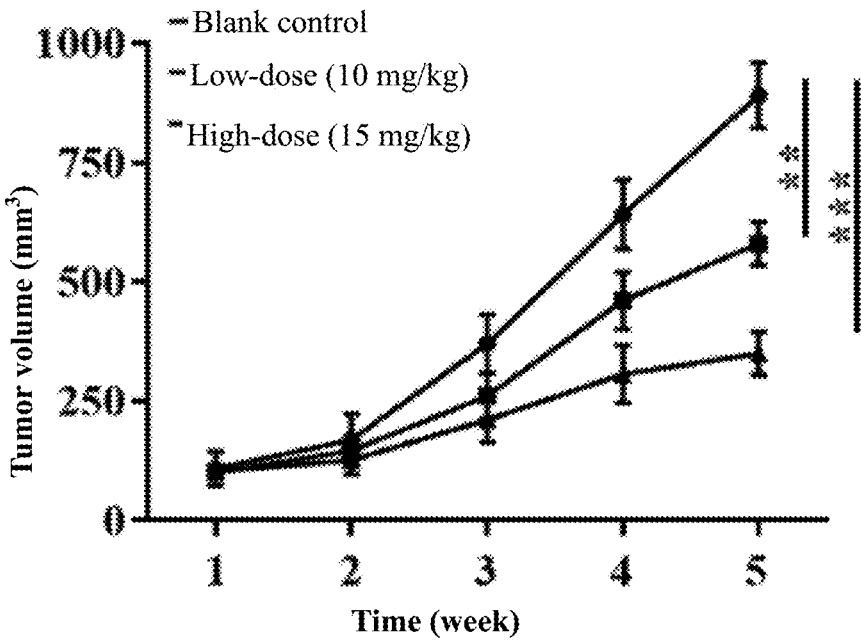
FIG. 11 shows the inhibitory effect of micropeptide HMMW on the tumor growth of SCC4 cells of human head and neck cancer in vivo in accordance with an embodiment.
Figure 12:
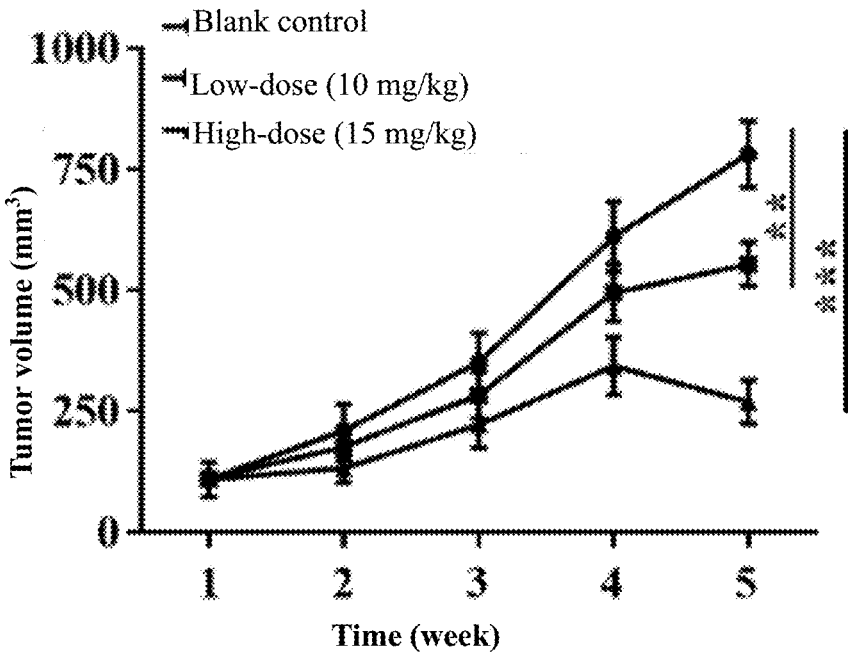
FIG. 12 shows the inhibitory effect of micropeptide HMMW on the tumor growth of SW579 cells of human thyroid cancer in vivo in accordance with an embodiment.
Figure 13:
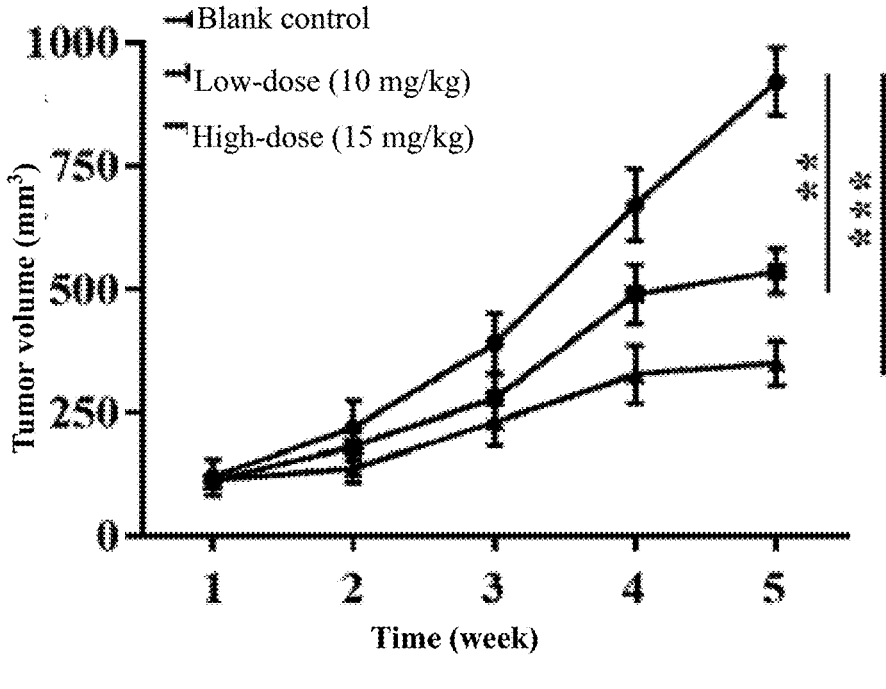
FIG. 13 shows the inhibitory effect of micropeptide HMMW on the tumor growth of A549 cells of human lung cancer in vivo in accordance with an embodiment.
Figure 14:
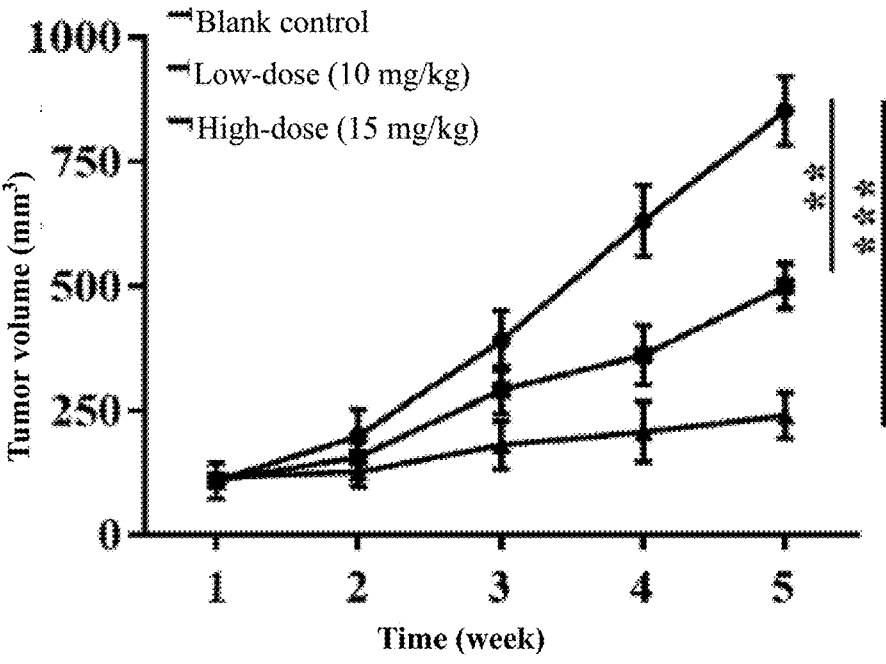
FIG. 14 shows the inhibitory effect of micropeptide HMMW on the tumor growth of TE13 cells of esophageal squamous cell carcinoma of human in vivo in accordance with an embodiment.
Figure 15:
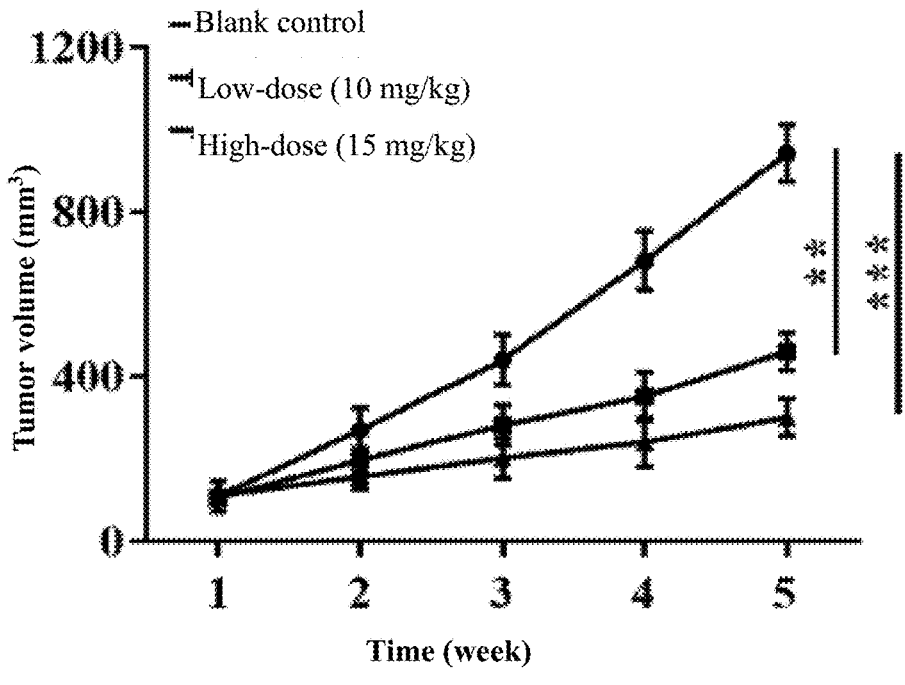
FIG. 15 shows the inhibitory effect of micropeptide HMMW on the tumor growth of MGC803 cells of human stomach cancer in vivo in accordance with an embodiment.
Figure 16:
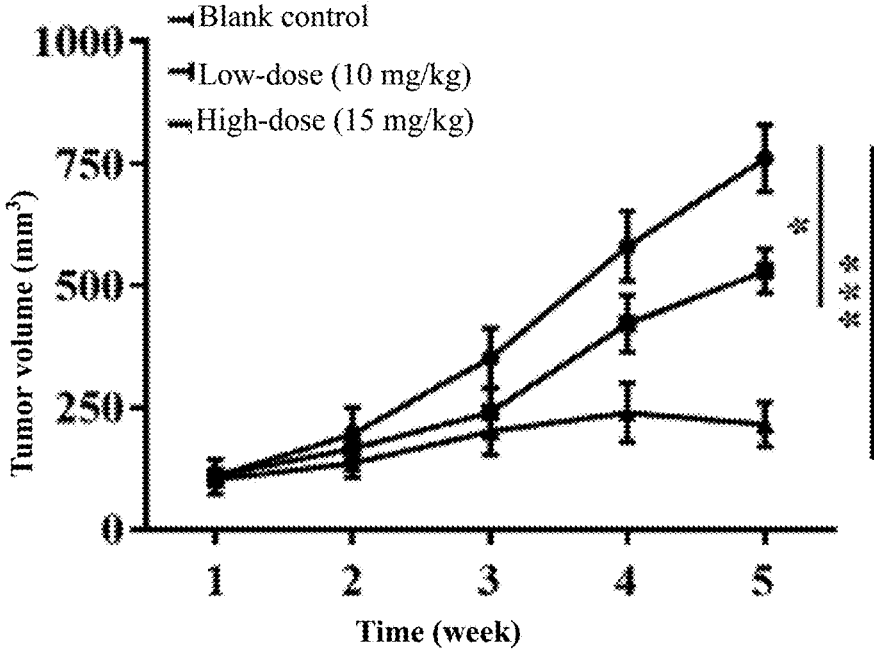
FIG. 16 shows the inhibitory effect of micropeptide HMMW on the tumor growth of MDA-MB-231 cells of human breast cancer in vivo in accordance with an embodiment.
Figure 17:
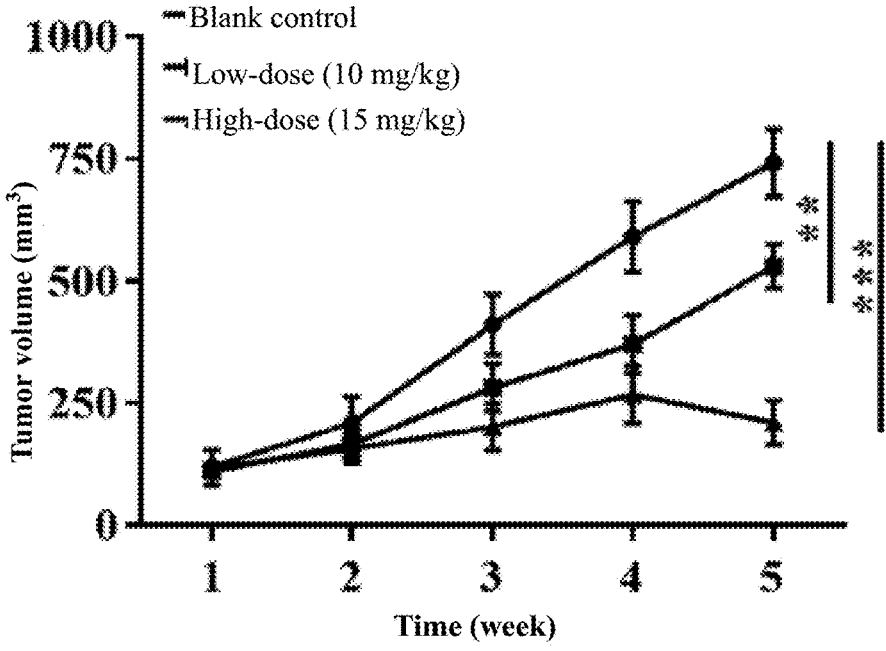
FIG. 17 shows the inhibitory effect of micropeptide HMMW on the tumor growth of UOK262 cells of human kidney cancer in vivo in accordance with an embodiment.
Figure 18:
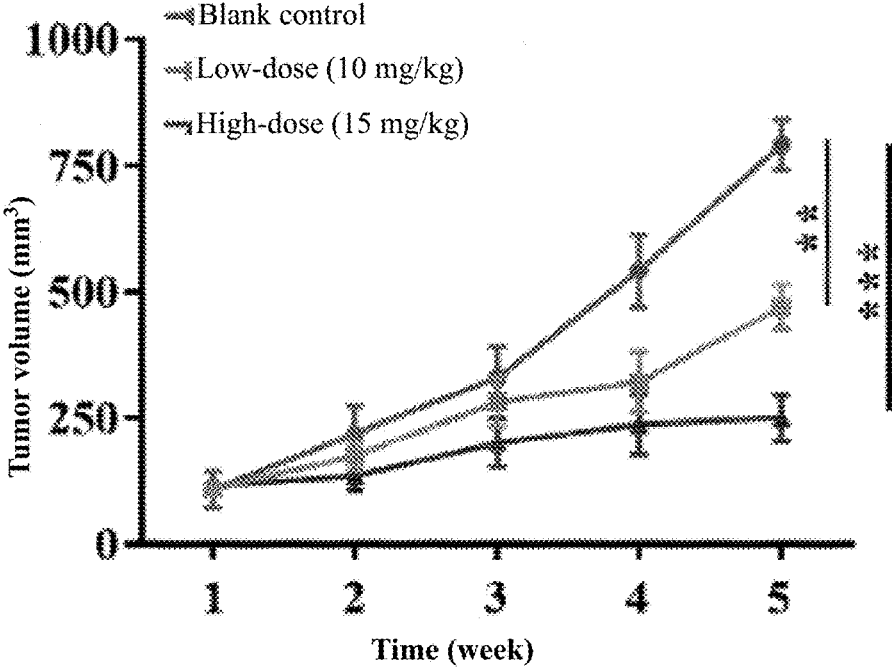
FIG. 18 shows the inhibitory effect of micropeptide HMMW on the tumor growth of A431 cells of human skin cancer in vivo in accordance with an embodiment.

Effects of Micropeptides HMMW I to IX on In Vivo Growth of Human Tumor Cells (1) Massively culture SCC4 cells of head and neck cancer, SW579 cells of thyroid cancer, A549 cells of lung The results are shown in FIG. 8. Compared with the normal saline control group, micropeptides HMMW I to IX could significantly inhibit the tumorigenicity in vivo of SCC4 cells of head and neck cancer, SW579 cells of thyroid cancer, A549 cells of lung cancer, TE13 cells of esophageal squamous cell carcinoma, MGC803 cells of stomach cancer, MDA-MB-231 cells of breast cancer, UOK262 cells of kidney cancer, and A431 cells of skin cancer of human and showed a dose-dependent relation. It indicates that the peptides with more than 85% homology to the original sequence HMMW I all have an inhibitory effect on the in vivo growth of tumor cells, so it can be considered to use micropeptides HMMW I to IX as a new type of antitumor peptides.

Embodiment 8

Expression of HMMW in Tumor Patients and Normal Para-Carcinoma Tissue

Download RNA-seq sequencing files and clinical information of cancer tissues and normal tissues of 16 tumors including head and neck cancer, brain glioma, thyroid cancer, esophageal squamous cell carcinoma, lung cancer, liver cancer, stomach cancer, kidney cancer, breast cancer, ovarian cancer, cervical cancer, bladder cancer, colorectal cancer, pancreatic cancer, osteosarcoma and skin cancer by the TCGA standard method, and analyze the differential expression of micropeptide HMMW (judgment criterion: (1)| Cancer/paracancer expression quantity |>2, (2)P<0.05).

TABLE 8

Analysis of expression quantity of micropeptide HMMW in human tumor tissue and normal tissue (cancer paracancer)

| Tumor type | Number of cases | Fold change in expressiot | Value P |
|---|---|---|---|
| Head and neck cancer | 528 | −20.895 | 6.13E−22 |
| Thyroid cancer | 507 | −8.285 | 4.05E−10 |
| Brain glioma | 516 | 1.394 | 0.0359 |
| Lung cancer | 504 | −12.345 | 1.38E−7 |
| Esophageal squamous cell carcinoma | 185 | −11.201 | 7.17E−5 |
| Ovarian cancer | 608 | 1.381 | 0.0683 |
| Cervical cancer | 307 | 0.984 | 0.0284 |
| Stomach cancer | 443 | −6.103 | 0.00018 |
| Breast cancer | 1098 | −8.193 | 2.48E−5 |
| Bladder cancer | 412 | 0.895 | 0.1935 |
| Liver cancer | 377 | 1.237 | 0.00014 |
| Osteosarcoma | 381 | 1.035 | 0.05213 |
| Stomach cancer | 291 | −19.351 | 4.15E−8 |
| Skin cancer | 470 | −15.245 | 0.00219 |
| Colorectal cancer | 461 | 0.818 | 0.0426 |
| Pancreatic cancer | 185 | 1.781 | 0.0503 |

As shown in Table 9, compared with normal tissues, the expression levels of micropeptide HMMW in eight tumor tissues of head and neck cancer, thyroid cancer, lung cancer, esophageal squamous cell carcinoma, gastric cancer, breast cancer, kidney cancer and skin cancer of human were significantly reduced. It indicates that the expression of micropeptide HMMW is significantly negatively correlated with the development of various tumors.

Embodiment 9

Expression of HMMW in Clinical Patients with Head and Neck Cancer and Normal Paracancer Tissues

(1) Collection of Specimens

With the informed consent of the patients, head and neck cancer and paracancer tissue specimens were collected during the operation, washed with normal saline, and stored in liquid nitrogen or −80° C. refrigerator for future use.

(2) Primer Design

Primer Premier5.0 was used to design primers according to the nucleotide sequence corresponding to the micropeptide HMMW, and the sequence is as follows:
Forward primer (the sequence is shown in SEQ ID NO: 3)
Reverse primer (the sequence is shown in SEQ ID NO: 4)

(3) Detection of HMMW Expression in Head and Neck Cancer Patients and Normal Paracancer Tissues by Real-Time Quantitative PCR Extract and collect the total RNA in the sample according to the Trizol manual of Life Technologies, then quantify the purity and concentration of the extracted RNA by the NanoDrop ND-1000 nucleic acid quantifier, and ensure the integrity of the extracted RNA through quality inspection by agarose. Use TaKaRa kit PrimeScript™ RT kit with gDNA Eraser (Perfect Real Time) to reversely transcribe the extracted total RNA to synthesize cDNA. Use TaKaRa kit SYBR® Premix Ex Taq™ II (TliRNaseH Plus) to conduct qPCR reaction. The reaction system is shown in the table below:

TABLE 9

PCR reaction system

| Reagent | Dose (µL) |
|---|---|
| SYBR Premix Ex Taq II (TliRNaseH Plus) (2×) | 12.5 |
| PCR Forward Primer (10 µM) | 1 |
| PCR Reverse Primer (10 µM) | 1 |
| DNA template (<100 ng) | 2 |
| Sterilized water | 8.5 |
| Total | 25 |

Figure 19:
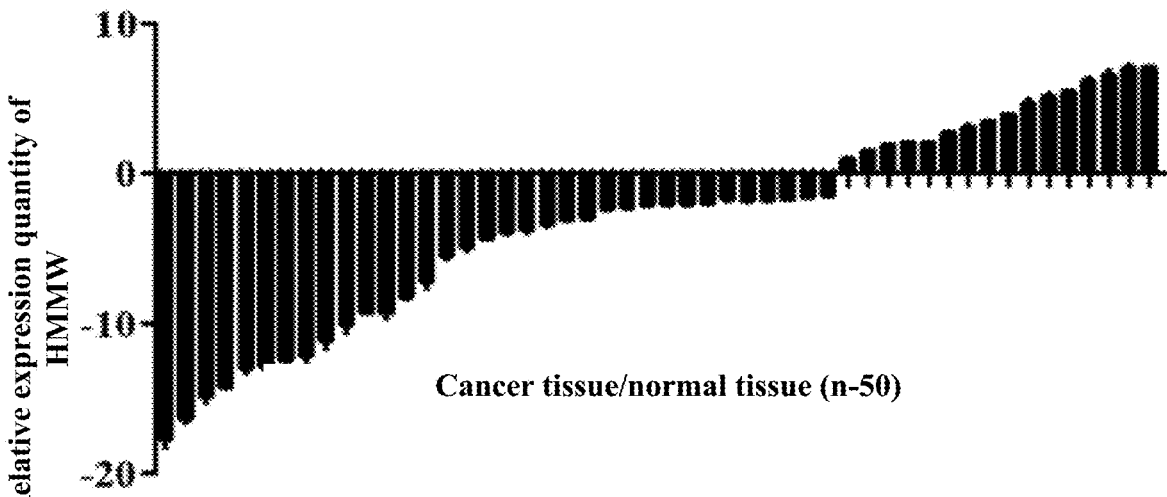
FIG. 19 shows the expression level of micropeptide HMMW in cancer tissue/normal tissue detected by the qPCR method in accordance with an embodiment.

After mixing the above components evenly, follow the procedure below: Initially denature at 95 DEG C. for 30 s at 40 cycles; 95 DEG C. for 5 s and 60 DEG C. for 30 s. Judge the specificity of the reaction according to the melting curve and calculate the relative expression quantity of HMMW by the $2^{-\Delta\Delta Ct}$ method. The result is shown in FIG. 19. In the head and neck cancer sample of about 75%, the expression level of HMMW was significantly lower than that of normal paracancer tissue.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. A method of preparing tumor treatment drugs, comprising:

utilizing a micropeptide HMMW, wherein the micropeptide HMMW comprises the amino acid sequence of SEQ ID NO: 1, and wherein the tumor is selected from the group consisting of: head and neck cancer, thyroid cancer, lung cancer, esophageal squamous cell carcinoma, stomach cancer, breast cancer, kidney cancer, and skin cancer of human.

* * * * *

SEQUENCE LISTING

<160> NUMBER OF SEQ ID NOS: 20

<210> SEQ ID NO 1
<211> LENGTH: 51

<212> TYPE: PRT
<213> ORGANISM: Artificial Sequence
<220> FEATURE:
<223> OTHER INFORMATION: synthesized

<400> SEQUENCE: 1

Met Glu Arg Ala Gly Val Pro Gly Phe Ser Pro Arg Arg Ser Ser Val
1               5                   10                  15

Glu Ala Lys Met Gln Ser Thr Ser Cys Ser Val Arg Lys Ser Ser Thr
            20                  25                  30

Val Thr Ala Trp Pro Ala Val Val Leu Leu Leu Ser Trp Gly Gln Arg
        35                  40                  45

Arg Gly Gly
    50

<210> SEQ ID NO 2
<211> LENGTH: 51
<212> TYPE: PRT
<213> ORGANISM: Artificial Sequence
<220> FEATURE:
<223> OTHER INFORMATION: synthesized

<400> SEQUENCE: 2

Met Glu Arg Ala Gly Val Pro Gly Phe Ser Pro Arg Arg Ser Ser Val
1               5                   10                  15

Glu Ala Lys Met Gln Ser Thr Ser Cys Ser Val Arg Lys Ser Ser Thr
            20                  25                  30

Val Thr Ala Trp Pro Ala Val Val Leu Leu Leu His Thr Ser Lys Asp
        35                  40                  45

Asp Glu Glu
    50

<210> SEQ ID NO 3
<211> LENGTH: 51
<212> TYPE: PRT
<213> ORGANISM: Artificial Sequence
<220> FEATURE:
<223> OTHER INFORMATION: synthesized

<400> SEQUENCE: 3

Met Gly Ser Thr Tyr Asn Lys Arg His Ser Pro Arg Arg Ser Ser Val
1               5                   10                  15

Glu Ala Lys Met Gln Ser Thr Ser Cys Ser Val Arg Lys Ser Ser Thr
            20                  25                  30

Val Thr Ala Trp Pro Ala Val Val Leu Leu Leu Ser Trp Gly Gln Arg
        35                  40                  45

Arg Gly Gly
    50

<210> SEQ ID NO 4
<211> LENGTH: 51
<212> TYPE: PRT
<213> ORGANISM: Artificial Sequence
<220> FEATURE:
<223> OTHER INFORMATION: synthesized

<400> SEQUENCE: 4

Met Glu Arg Ala Gly Val Pro Gly Phe Ser Pro Arg Arg Ser Ser Val
1               5                   10                  15

Glu Ala Lys Met Gln Ser Thr Ser Cys Ser Val Arg Lys Ser Ser Thr
            20                  25                  30

```
Val Thr Ala Trp Pro Ala Val Val Leu Leu Leu Ser Trp Gly Lys Asp
        35                  40                  45

Asp Glu Glu
    50

<210> SEQ ID NO 5
<211> LENGTH: 51
<212> TYPE: PRT
<213> ORGANISM: Artificial Sequence
<220> FEATURE:
<223> OTHER INFORMATION: synthesized

<400> SEQUENCE: 5

Met Gly Ser Thr Tyr Asn Pro Gly Phe Ser Pro Arg Arg Ser Ser Val
1               5                  10                  15

Glu Ala Lys Met Gln Ser Thr Ser Cys Ser Val Arg Lys Ser Ser Thr
            20                  25                  30

Val Thr Ala Trp Pro Ala Val Val Leu Leu Leu Ser Trp Gly Gln Arg
        35                  40                  45

Arg Gly Gly
    50

<210> SEQ ID NO 6
<211> LENGTH: 51
<212> TYPE: PRT
<213> ORGANISM: Artificial Sequence
<220> FEATURE:
<223> OTHER INFORMATION: synthesized

<400> SEQUENCE: 6

Met Glu Arg Ala Gly Val Pro Gly Phe Ser Pro Arg Arg Ser Ser Val
1               5                  10                  15

Glu Ala Lys Met Gln Ser Thr Ser Cys Ser Val Arg Lys Ser Ser Thr
            20                  25                  30

Val Thr Ala Trp Pro Ala Val Val Leu Leu Leu Ser Trp Gly Gln Arg
        35                  40                  45

Asp Glu Glu
    50

<210> SEQ ID NO 7
<211> LENGTH: 51
<212> TYPE: PRT
<213> ORGANISM: Artificial Sequence
<220> FEATURE:
<223> OTHER INFORMATION: synthesized

<400> SEQUENCE: 7

Met Gly Ser Thr Gly Val Pro Gly Phe Ser Pro Arg Arg Ser Ser Val
1               5                  10                  15

Glu Ala Lys Met Gln Ser Thr Ser Cys Ser Val Arg Lys Ser Ser Thr
            20                  25                  30

Val Thr Ala Trp Pro Ala Val Val Leu Leu Leu Ser Trp Gly Gln Arg
        35                  40                  45

Arg Gly Gly
    50

<210> SEQ ID NO 8
<211> LENGTH: 51
<212> TYPE: PRT
<213> ORGANISM: Artificial Sequence
<220> FEATURE:
<223> OTHER INFORMATION: synthesized
```

-continued

<400> SEQUENCE: 8

Met Glu Arg Ala Gly Val Pro Gly Phe Ser Pro Arg Arg Ser Ser Val
1               5                   10                  15

Glu Ala Lys Met Gln Ser Thr Ser Cys Ser Val Arg Lys Ser Ser Thr
            20                  25                  30

Val Thr Ala Trp Pro Ala Val Val Leu Leu Leu Ser Trp Gly Gln Arg
        35                  40                  45

Arg Gly Glu
    50

<210> SEQ ID NO 9
<211> LENGTH: 51
<212> TYPE: PRT
<213> ORGANISM: Artificial Sequence
<220> FEATURE:
<223> OTHER INFORMATION: synthesized

<400> SEQUENCE: 9

Met Gly Arg Ala Gly Val Pro Gly Phe Ser Pro Arg Arg Ser Ser Val
1               5                   10                  15

Glu Ala Lys Met Gln Ser Thr Ser Cys Ser Val Arg Lys Ser Ser Thr
            20                  25                  30

Val Thr Ala Trp Pro Ala Val Val Leu Leu Leu Ser Trp Gly Gln Arg
        35                  40                  45

Arg Gly Gly
    50

<210> SEQ ID NO 10
<211> LENGTH: 156
<212> TYPE: PRT
<213> ORGANISM: Artificial Sequence
<220> FEATURE:
<223> OTHER INFORMATION: synthesized

<400> SEQUENCE: 10

Ala Thr Gly Gly Ala Gly Ala Gly Ala Gly Cys Ala Gly Gly Gly Gly
1               5                   10                  15

Thr Gly Cys Cys Cys Gly Gly Gly Thr Thr Cys Thr Cys Thr Cys Cys
            20                  25                  30

Gly Cys Gly Gly Cys Gly Cys Thr Cys Ala Thr Cys Gly Gly Thr Gly
        35                  40                  45

Gly Ala Gly Gly Cys Gly Ala Ala Gly Ala Thr Gly Cys Ala Gly Ala
    50                  55                  60

Gly Cys Ala Cys Cys Ala Gly Cys Thr Gly Cys Ala Gly Thr Gly Thr
65                  70                  75                  80

Cys Ala Gly Gly Ala Ala Gly Ala Gly Cys Thr Cys Cys Ala Cys Ala
                85                  90                  95

Gly Thr Cys Ala Cys Cys Gly Cys Cys Thr Gly Gly Cys Cys Ala Gly
            100                 105                 110

Cys Cys Gly Thr Cys Gly Thr Gly Cys Thr Gly Thr Thr Gly Cys Thr
            115                 120                 125

Gly Ala Gly Cys Thr Gly Gly Gly Gly Ala Cys Ala Gly Ala Gly Ala
        130                 135                 140

Ala Gly Ala Gly Gly Cys Gly Gly Ala Thr Gly Ala
145                 150                 155

<210> SEQ ID NO 11

```
<211> LENGTH: 156
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t

<400> SEQUENCE: 11
atggagagag caggggtgcc cgggttctct ccgcggcgct catcggtgga ggcgaagatg      60
cagagcacca gctgcagtgt caggaagagc tccacagtca ccgcctggcc agccgtcgtg     120
ctgttgctgc acacntcnaa agacgacgaa gagtga                               156

<210> SEQ ID NO 12
<211> LENGTH: 156
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 12
atgggntcna cntataataa acgncactct ccgcggcgct catcggtgga ggcgaagatg      60
cagagcacca gctgcagtgt caggaagagc tccacagtca ccgcctggcc agccgtcgtg     120
ctgttgctga gctggggaca gagaagaggc ggatga                               156

<210> SEQ ID NO 13
<211> LENGTH: 156
<212> TYPE: DNA
<213> ORGANISM: Artificial Sequence
<220> FEATURE:
<223> OTHER INFORMATION: synthesized

<400> SEQUENCE: 13
atggagagag caggggtgcc cgggttctct ccgcggcgct catcggtgga ggcgaagatg      60
cagagcacca gctgcagtgt caggaagagc tccacagtca ccgcctggcc agccgtcgtg     120
ctgttgctga gctggggaaa agacgacgaa gagtga                               156

<210> SEQ ID NO 14
<211> LENGTH: 156
<212> TYPE: DNA
<213> ORGANISM: Artificial Sequence
<220> FEATURE:
<223> OTHER INFORMATION: synthesized
<220> FEATURE:
<221> NAME/KEY: misc_feature
```

-continued

```
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 14
atgggntcna cntataatcc cgggttctct ccgcggcgct catcggtgga ggcgaagatg      60
cagagcacca gctgcagtgt caggaagagc tccacagtca ccgcctggcc agccgtcgtg     120
ctgttgctga gctggggaca gagaagaggc ggatga                              156

<210> SEQ ID NO 15
<211> LENGTH: 156
<212> TYPE: DNA
<213> ORGANISM: Artificial Sequence
<220> FEATURE:
<223> OTHER INFORMATION: synthesized

<400> SEQUENCE: 15
atggagagag caggggtgcc cgggttctct ccgcggcgct catcggtgga ggcgaagatg      60
cagagcacca gctgcagtgt caggaagagc tccacagtca ccgcctggcc agccgtcgtg     120
ctgttgctga gctggggaca gagagacgaa gagtga                              156

<210> SEQ ID NO 16
<211> LENGTH: 156
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 16
atgggntcna cngggdtgcc cgggttctct ccgcggcgct catcggtgga ggcgaagatg      60
cagagcacca gctgcagtgt caggaagagc tccacagtca ccgcctggcc agccgtcgtg     120
ctgttgctga gctggggaca gagaagaggc ggatga                              156

<210> SEQ ID NO 17
<211> LENGTH: 156
<212> TYPE: DNA
<213> ORGANISM: Artificial Sequence
<220> FEATURE:
<223> OTHER INFORMATION: synthesized

<400> SEQUENCE: 17
atggagagag caggggtgcc cgggttctct ccgcggcgct catcggtgga ggcgaagatg      60
cagagcacca gctgcagtgt caggaagagc tccacagtca ccgcctggcc agccgtcgtg     120
ctgttgctga gctggggaca gagaagaggc gagtga                              156
```

-continued

```
<210> SEQ ID NO 18
<211> LENGTH: 156
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (6)..(6)
<223> OTHER INFORMATION: n is a, c, g, or t

<400> SEQUENCE: 18
atgggnagag caggggtgcc cgggttctct ccgcggcgct catcggtgga ggcgaagatg      60
cagagcacca gctgcagtgt caggaagagc tccacagtca ccgcctggcc agccgtcgtg     120
ctgttgctga gctggggaca gagaagaggc ggatga                              156

<210> SEQ ID NO 19
<211> LENGTH: 22
<212> TYPE: DNA
<213> ORGANISM: Artificial Sequence
<220> FEATURE:
<223> OTHER INFORMATION: synthesized

<400> SEQUENCE: 19
atggagagag caggggtgcc cg                                              22

<210> SEQ ID NO 20
<211> LENGTH: 23
<212> TYPE: DNA
<213> ORGANISM: Artificial Sequence
<220> FEATURE:
<223> OTHER INFORMATION: synthesized

<400> SEQUENCE: 20
cgcctcttct ctgtccccag ctc                                            23
```